US010252253B2

United States Patent
Miyajima et al.

(10) Patent No.: US 10,252,253 B2
(45) Date of Patent: Apr. 9, 2019

(54) G-$C_3N_4$ FILM

(71) Applicant: RIKEN, Saitama (JP)

(72) Inventors: Daigo Miyajima, Saitama (JP); Hiroki Arazoe, Saitama (JP); Masuki Kawamoto, Saitama (JP); Kouki Akaike, Saitama (JP); Yoshiko Koizumi, Saitama (JP); Takuzo Aida, Saitama (JP)

(73) Assignee: RIKEN, Saitama (JP)

( * ) Notice: Subject to any disclaimer, the term of this patent is extended or adjusted under 35 U.S.C. 154(b) by 436 days.

(21) Appl. No.: 14/653,641

(22) PCT Filed: Dec. 24, 2013

(86) PCT No.: PCT/JP2013/084543
§ 371 (c)(1),
(2) Date: Jun. 18, 2015

(87) PCT Pub. No.: WO2014/098251
PCT Pub. Date: Jun. 26, 2014

(65) Prior Publication Data
US 2015/0352539 A1 Dec. 10, 2015

(30) Foreign Application Priority Data

Dec. 21, 2012 (JP) .................. 2012-280283

(51) Int. Cl.
*B01J 31/06* (2006.01)
*B01J 35/02* (2006.01)
(Continued)

(52) U.S. Cl.
CPC .............. *B01J 31/06* (2013.01); *B01J 27/24* (2013.01); *B01J 35/002* (2013.01); *B01J 35/004* (2013.01);
(Continued)

(58) Field of Classification Search
None
See application file for complete search history.

(56) References Cited

U.S. PATENT DOCUMENTS 5,606,056 A * 2/1997 Kouvetakis ......... C01B 21/0605
428/408
6,428,762 B1 * 8/2002 Khabashesku ......... B82Y 30/00
423/384

FOREIGN PATENT DOCUMENTS

CN 103272639 9/2013
JP 2012-250884 12/2012

OTHER PUBLICATIONS

Li et al, "Electrodeposition route to prepare graphite-like carbon nitride," Materials Science and Engineering B, vol. 106 (2004) pp. 308-312.*

(Continued)

*Primary Examiner* — Guinever S Gregorio
(74) *Attorney, Agent, or Firm* — Casimir Jones, S.C.; Robert A. Goetz

(57) ABSTRACT

In order to provide g-$C_3N_4$ capable of being simply and easily handled, a g-$C_3N_4$ film is produced by heating, as a starting material, a compound represented by $X^+_m Y^{m-}$, wherein $X^+$ is a guanidium ion or the like ion, and $Y^{m-}$ is an anion, to vaporize the compound or its reactant, and depositing the compound or the reactant over a surface of a base material heated, the surface carrying negative electric charges or having π electrons, so that the compound or the reactant is polymerized on the base material to generate g-$C_3N_4$.

7 Claims, 10 Drawing Sheets

(51) Int. Cl.
*B01J 37/02* (2006.01)
*B01J 37/08* (2006.01)
*C01B 3/04* (2006.01)
*C07D 487/16* (2006.01)
*C23C 16/01* (2006.01)
*C23C 16/34* (2006.01)
*C01B 21/06* (2006.01)
*B01J 27/24* (2006.01)
*B01J 35/00* (2006.01)
*H01M 4/58* (2010.01)
*H01M 4/587* (2010.01)
*C01B 13/02* (2006.01)
*C25B 11/04* (2006.01)
*C25B 1/00* (2006.01)
*C25B 1/04* (2006.01)

(52) U.S. Cl.
CPC .......... *B01J 35/02* (2013.01); *B01J 37/0219* (2013.01); *B01J 37/08* (2013.01); *C01B 3/042* (2013.01); *C01B 13/0207* (2013.01); *C01B 21/0605* (2013.01); *C07D 487/16* (2013.01); *C23C 16/01* (2013.01); *C23C 16/347* (2013.01); *C25B 1/003* (2013.01); *C25B 1/04* (2013.01); *C25B 11/04* (2013.01); *H01M 4/58* (2013.01); *H01M 4/587* (2013.01); *B01J 2231/62* (2013.01); *B01J 2531/002* (2013.01); *B01J 2531/008* (2013.01); *C01P 2006/40* (2013.01); *C01P 2006/60* (2013.01); *Y02E 60/364* (2013.01); *Y02E 60/366* (2013.01)

(56) References Cited

OTHER PUBLICATIONS

International preliminary report on patentability, International Patent Application No. PCT/JP2013/084543, dated Jul. 2, 2015, six pages.

International Search Report, International Patent Application No. PCT/JP2013/084543, dated Apr. 1, 2014, two pages.

Wang et al., "Boron- and Fluorine-Containing Mesoporous Carbon Nitride Polymers: Metal-Free Catalysts for Cyclohexane Oxidation." Angew Chem Int Ed Engl. Apr. 26, 2010;49(19):3356-9.

Talapaneni et al., "Synthesis of nitrogen-rich mesoporous carbon nitride with tunable pores, band gaps and nitrogen content from a single aminoguanidine precursor." ChemSusChem. Apr. 2012;5(4):700-8, Abstract.

Yang et al., "Metal-Free Photocatalytic Graphitic Carbon Nitride on p-Type Chalcopyrite as a Composite Photocathode for Light-Induced Hydrogen Evolution." ChemSusChem. Jul. 2012;5(7):1227-32, Abstract.

Braml et al., "Formation of Melamium Adducts by Pyrolysis of Thiourea or Melamine/NH4Cl Mixtures." Eur. J. 2012, 18, 1811-1819.

Zhang et al., "Polycondensation of thiourea into carbon nitride semiconductors as visible light photocatalysts." Chem. 2012, 22, 8083-8091.

Bojdys et al., "Ionothermal synthesis of crystalline, condensed, graphitic carbon nitride." Chemistry. 2008;14 (27):8177-82.

Liu et al., "Simple pyrolysis of urea into graphitic carbon nitride with recyclable adsorption and photocatalytic activity." W.J. Mater. Chem. 2011, 21, 14398-14401.

Yan H., "Soft-templating synthesis of mesoporous graphitic carbon nitride with enhanced photocatalytic H2 evolution under visible light." Chem. Commun., 2012, 48, 3430-3432.

Maeda et al., "Photocatalytic Activities of Graphitic Carbon Nitride Powder for Water Reduction and Oxidation under Visible Light." J. Phys. Chem. C, 2009, 113 (12), pp. 4940-4947.

Wang et al., "A metal-free polymeric photocatalyst for hydrogen production from water under visible light." Nature Materials, 2009, 5, 76-80.

* cited by examiner

G-C₃N₄ FILM

TECHNICAL FIELD

The present invention relates to a method for producing a graphitic carbon nitride (g-$C_3N_4$) film, a g-$C_3N_4$ film produced by the method, and a use of the g-$C_3N_4$ film.

BACKGROUND ART

Organic photocatalysts composed of ubiquitous elements such as carbon and nitrogen have attracted attention as environment-friendly and resource-conscious materials. Graphitic carbon nitride (g-$C_3N_4$), which is a polymer that produces hydrogen through water photolysis (Non-Patent Literature 1), is a heterogeneous organic photocatalyst excellent in light resistance. A hydrogen production process in which fossil fuel is used as a starting material produces carbon dioxide in the production process. On the contrary, a hydrogen production process carried out through water photolysis by g-$C_3N_4$ produces no carbon dioxide. Such a process allows providing environment-friendly clean energy.

For example, g-$C_3N_4$ can be produced as a water-insoluble powdery polymer by consecutive polymerization of a monomer such as, for example, cyanamide (Non-Patent Literature 2), melamine (Non-Patent Literature 3), urea (Non-Patent Literature 4), thiourea (Non-Patent Literature 6), or dicyandiamide (Non-Patent Literature 5). Non-Patent Literature 7 discloses performing spin-coating with a solution of dicyandiamide and then heating the spin-coated dicyandiamide to obtain g-$C_3N_4$ in sheet form.

CITATION LIST

Non-Patent Literatures

Non-patent Literature 1
Wang, X; Maeda, K.; Thomas, A.; Takanabe, K.; Xin, G.; Carlsson, J. M.; Domen, K.; Antonietti, M. Nature Mater. 2009, 5, 76-80.

Non-patent Literature 2
Maeda, K.; Wang, X.; Nishihara, Y.; Lu, D.; Antonietti, M.; Domen, K. J. Phys. Chem. B 2009, 113, 4940-4947.

Non-patent Literature 3
Yan, H. Chem. Commun. 2012, 48, 3430-3432.

Non-patent Literature 4
Liu, J.; Zhang, T.; Wang, Z.; Dawsona, G.; Chen, W. J. Mater. Chem. 2011, 21, 14398-14401.

Non-patent Literature 5
Bojdys, M. J.; Muller, J. -O.; Antonietti, M.; Thomas, A. Chem. Eur. J. 2008, 14, 8177-8182.

Non-patent Literature 6 Zhang, G.; Zhang, J.; Zhang, M.; Wang, X. J. Mater. Chem. 2012, 22, 8083-8091.

Non-patent Literature 7
Yang, F.; Lublow, M.; Orthmann, S.; Merschjann, C.; Tyborski, T.; Rusu, M.; Kubala, S.; Thomas, A.; Arrigo, R.; Havecker, M.; Schedel-Niedrig, T. Chem. Sus. Chem. 2012, 5, 1227-1232.

Non-patent Literature 8
Braml, N. E.; Sattler, A.; Schnick, W. Chem. Eur. J. 2012, 18, 1811-1819.

SUMMARY OF INVENTION

Technical Problem

The advantage of the heterogeneous photocatalyst is the ability of simply producing hydrogen through light irradiation of a powdery catalyst dispersed in water. However, the powdery catalyst needs to be separated and recovered from the water after use. Therefore, from the viewpoint of practical use, there is a demand for g-$C_3N_4$ capable of being simply and easily handled. Note that the g-$C_3N_4$ production method disclosed in Non-Patent Literature 7 has difficulty in obtaining a sheet of practically adequate quality.

The present invention has been achieved to solve the above problems, and it is one of the objects of the present invention to provide g-$C_3N_4$ capable of being simply and easily handled.

Solution to Problem

A method for producing a graphitic carbon nitride film (g-$C_3N_4$ film) according to the present invention includes the steps of: heating, as a starting material, a compound represented by $X^+_m Y^{m-}$, wherein $X^+$ is selected from a guanidium ion, a melaminium ion, a melamium ion, a melemium ion, a guanidine derivative ion represented by Formula (I) below, and a guanidine derivative ion represented by Formula (II) below, $Y^{m-}$ is an anion, and m is a valence of Y,

[Chem. 1]

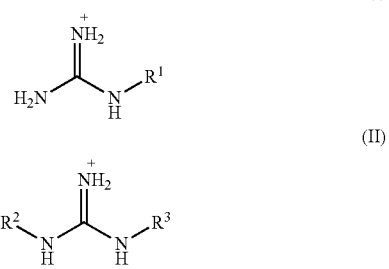

wherein, in Formulae (I) and (II), $R^1$, $R^2$, and $R^3$ are independently selected from an amino group, a nitro group, an alkyl group having 1 to 10 carbon atoms, —$(C_2H_4O)_n$—$R^4$ (where n is 1 to 10, and $R^4$ is an alkyl group having 1 to 4 carbon atoms), halogen, and a primary amide group, to vaporize the compound or its reactant; and depositing the compound or the reactant over a surface of a base material heated, the surface carrying negative electric charges or having π electrons, so that the compound or the reactant is polymerized on the base material to generate a graphitic carbon nitride.

Still further, the present invention provides a method for producing g-$C_3N_4$, the method including the steps of: heating, as a starting material, a compound represented by $X^+_2CO_3^{2-}$ or $X^+CH_3COO^-$, wherein $X^+$ is selected from a guanidium ion, a melaminium ion, a melamium ion, a melemium ion, a guanidine derivative ion represented by Formula (I) above, and a guanidine derivative ion represented by Formula (II) above, to polymerize the compound, thereby generating a graphitic carbon nitride.

Yet further, the present invention provides a g-$C_3N_4$ film having a single-layer or multilayer sheet structure.

Further, the present invention provides a g-$C_3N_4$ film having a sheet structure in which melem structural units are crosslinked in two-dimensional directions, wherein a peak obtained for the g-$C_3N_4$ film by out-of-plane X-ray diffraction is derived from a sheet-to-sheet distance only.

Still further, the present invention provides a g-$C_3N_4$ film that produces a photocurrent of not less than 0.8 μA/cm² when the g-$C_3N_4$ film is irradiated with visible light of not less than 420 nm while a constant voltage of 0.2 V is applied to the g-$C_3N_4$ film.

Yet further, the present invention provides a g-$C_3N_4$ film having transparency.

ADVANTAGEOUS EFFECTS OF INVENTION

The present invention makes it possible to form g-$C_3N_4$ in film form. Further, the present invention makes it possible to form and fix the g-$C_3N_4$ in film form onto a base material such as a substrate. Thus, the g-$C_3N_4$ in film form, when used as a catalyst, does not necessarily have to be dispersed in water. This allows simple and easy recovery of the g-$C_3N_4$ from the water after use.

DESCRIPTION OF EMBODIMENTS

[Method for Producing g-$C_3N_4$ Film]

Figure 1:
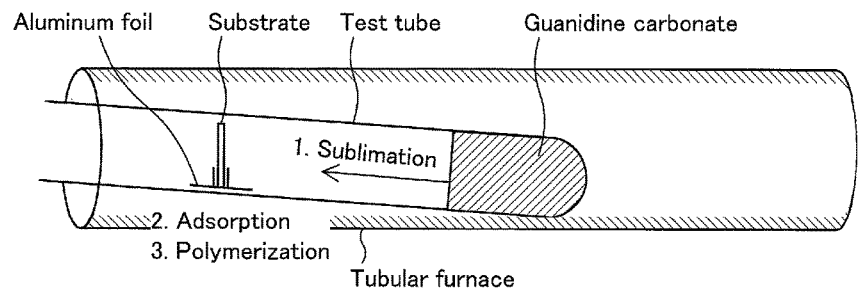
FIG. 1 is a schematic view illustrating an apparatus used in Example 1.

A method for producing a g-$C_3N_4$ (graphitic carbon nitride) film according to the present invention includes the steps of: heating, as a starting material, a compound represented by $X^+_m Y^{m-}$, wherein $X^+$ is selected from a guanidium ion, a melaminium ion, a melamium ion, a melemium ion, a guanidine derivative ion represented by Formula (I) below, and a guanidine derivative ion represented by Formula (II) below, $Y^{m-}$ is an anion, and m is a valence of Y, to vaporize the compound or its reactant; and depositing the compound or the reactant over a surface of a base material heated, the surface carrying negative electric charges or having π electrons, so that the compound or the reactant is polymerized on the base material to generate a graphitic carbon nitride.

(Starting Material)

A compound used as a starting material is a compound represented by $X^+_m Y^{m-}$ (referred to as "compound $X^+_m Y^{m-}$") where $X^+$ is selected from a guanidium ion, a melaminium ion, a melamium ion, a melemium ion, a guanidine derivative ion represented by Formula (I) below, and a guanidine derivative ion represented by Formula (II) below.

[Chem. 2]

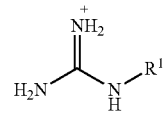

(I)

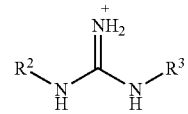

(II)

In the above Formula (I), $R^1$ is selected from an amino group, a nitro group, an alkyl group having 1 to 10 carbon atoms, preferably 1 to 5 carbon atoms, and more preferably 1 to 3 carbon atoms, —$(C_2H_4O)_n$—$R^4$, halogen, and a primary amide group. In —$(C_2H_4O)_n$—$R^4$, n is 1 to 10, preferably 1 to 5, and more preferably 1 to 3, and $R^4$ is an alkyl group having 1 to 4 carbon atoms. In —$(C_2H_4O)_n$—$R^4$, —$(C_2H_4O)_n$ is an ethylene oxide group having a carbon atom which is to be bound to a nitrogen atom of a guanidine. Examples of the alkyl group having 1 to 10 carbon atoms include a methyl group, an ethyl group, a propyl group, a butyl group, an isobutyl group, and the like. The halogen includes fluorine, chlorine, bromine, and iodine. $R^1$ is preferably selected from an amino group and a nitro group.

In the above Formula (II), $R^2$ and $R^3$ are independently selected from an amino group, a nitro group, an alkyl group having 1 to 10 carbon atoms, preferably 1 to 5 carbon atoms, and more preferably 1 to 3 carbon atoms, —$(C_2H_4O)_n$—$R^4$, halogen, and a primary amide group. Explanations of —$(C_2H_4O)_n$—$R^4$ and the halogen are the same as those in the above Formula (I). Preferably, $R^2$ and $R^3$ are independently selected from the amino group and the nitro group.

The guanidium ion, the melaminium ion, the melamium ion, and the melemium ion respectively have the following structures:

[Chem. 3]

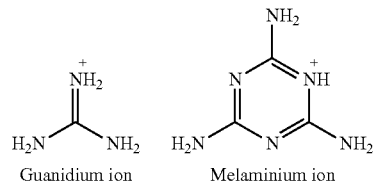

Guanidium ion    Melaminium ion

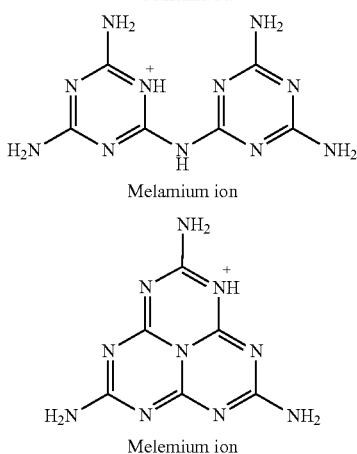

Melamium ion

Melemium ion $X^+_m$ is preferably selected from the guanidium ion, the melaminium ion, the melamium ion, and the melemium ion. More preferably, $X^+_m$ is the guanidium ion.

In $X^+_m Y^{m-}$, $Y^{m-}$ is an anion, and m is a valence of Y. Examples of the anion include $CO_3^{2-}$, $SO_4^{2-}$, $Cl^-$, $HPO_4^{2-}$, $NO_3^-$, $SCN^-$, $SO_3NH_3^-$, $CrO_4^{2-}$, p-toluenesulfonate, $ReO_4^-$, $R^5COO^-$, and the like. In $R^5CO^-$, $R^5$ is not limited to any specific group, but is preferably a low molecular weight group. Examples of $R^5$ include an alkyl group, an alkenyl group, an alkynyl group, a halogenated alkyl group, a carboxy group, a carboxyalkyl group ($-(CH_2)1COOH$) each of which has 1 to 10 carbon atoms, preferably 1 to 5 carbon atoms, and more preferably 1 to 3 carbon atoms, a phenyl group which may have a substituent, and the like. Examples of the substituent of the phenyl group include an alkyl group having 1 to 5 carbon atoms, a carboxy group, and the like. Specifically, $R^5$ includes the followings:

[Chem. 4]

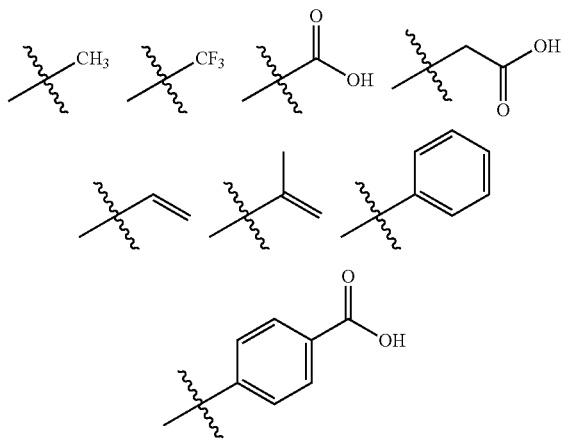

$Y^{m-}$ is preferably selected from $CO_3^{2-}$, $SO_4^{2-}$, $Cl^-$, and $R^5COO^-$ and is more preferably selected from $CO_3^{2-}$ and $R^5COO^-$, i.e. an anion represented by Formula (III) below (where $R^6$ is selected from $O^-$ and $R^5$). $Y^{m-}$ is further preferably selected from $CO_3^{2-}$ and $CH_3COO^-$ and is particularly preferably $CO_3^{2-}$.

[Chem. 5]

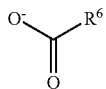

(III)

In a case where $Y^{m-}$ is $CO_3^{2-}$, the compound $X^+_m Y^{m-}$ has no melting point. Thus, it is considered that $CO_3^{2-}$ is less likely to escape from a system before the compound $X^+_m Y^{m-}$ or its reactant is vaporized. Therefore, in a case where $Y^{m-}$ is $CO_3^{2-}$, the compound $X^+_m Y^{m-}$ or its reactant is vaporized in larger amount, as compared to a case where $Y^{m-}$ is not $CO_3^{2-}$. Consequently, it is considered that it is possible to produce a film more efficiently.

The compound represented by $X^+_m Y^{m-}$ can be preferably a salt of guanidine and acid from the viewpoint of easy availability. From the viewpoint of the efficiency in producing a g-$C_3N_4$ film, the compound represented by $X^+_m Y^{m-}$ is more preferably selected from guanidine carbonate, guanidine sulfate, guanidine hydrochloride, and guanidine acetate, further preferably selected from guanidine carbonate and guanidine acetate, and particularly preferably guanidine carbonate.

The compound represented by $X^+_m Y^{m-}$ may be the one commercially available or may be synthesized by a known method. Further, the compound represented by $X^+_m Y^{m-}$ may be a mixture of plural kinds of compounds or may be mixed with other compound from which g-$C_3N_4$ can be formed.

(Base Material)

A base material used in the production method of the present invention has a surface carrying negative electric charges or having π electrons.

The negative electric charges carried by the base material may be the ones originally possessed by the base material or may be artificially given to the base material. Examples of the base material having a surface carrying negative electric charges include glass, quartz glass, indium tin oxide (ITO) glass, fluorine-doped tin oxide (FTO) glass, silicon, a metallic material, an inorganic semiconductor, and the like.

Examples of the base material having a surface having π electrons include graphite, a fullerene, a carbon nanotube, glassy carbon, other carbon materials (e.g. a carbon fiber and a carbon rod), and the like. Examples of the graphite include highly oriented pyrolytic graphite (HOPG).

Further, it is preferable that the base material has heat resistance because the base material is heated for polymerization reaction into g-$C_3N_4$. The degree of heat resistance of the base material is determined according to a heating temperature, a heating time, and other conditions. The base material is preferably the one that is resistant to heat of, for example, 700° C., and more preferably the one that is resistant to heat of 1000° C. Note that a base material having a desired heat resistance can be easily selected by a person skilled in the art.

The size and shape of the base material are not limited to specific ones. The base material can preferably be such that the surface carrying negative electric charges or having π electrons is a flat surface. More preferably, the base material can be a substrate.

(Details of the Production Method)

The aforementioned compound used as the starting material is subjected to heat so that the compound or its reactant is vaporized. The term "its reactant" refers to a product into which the compound used as the starting material is transformed through reaction when heated, the product being a compound different in structure from the compound used as the starting material. For example, guanidine carbonate, which can be used as the starting material, is expected to transform, when heated, according to the following scheme (see Reference Example described later).

[Chem. 6]
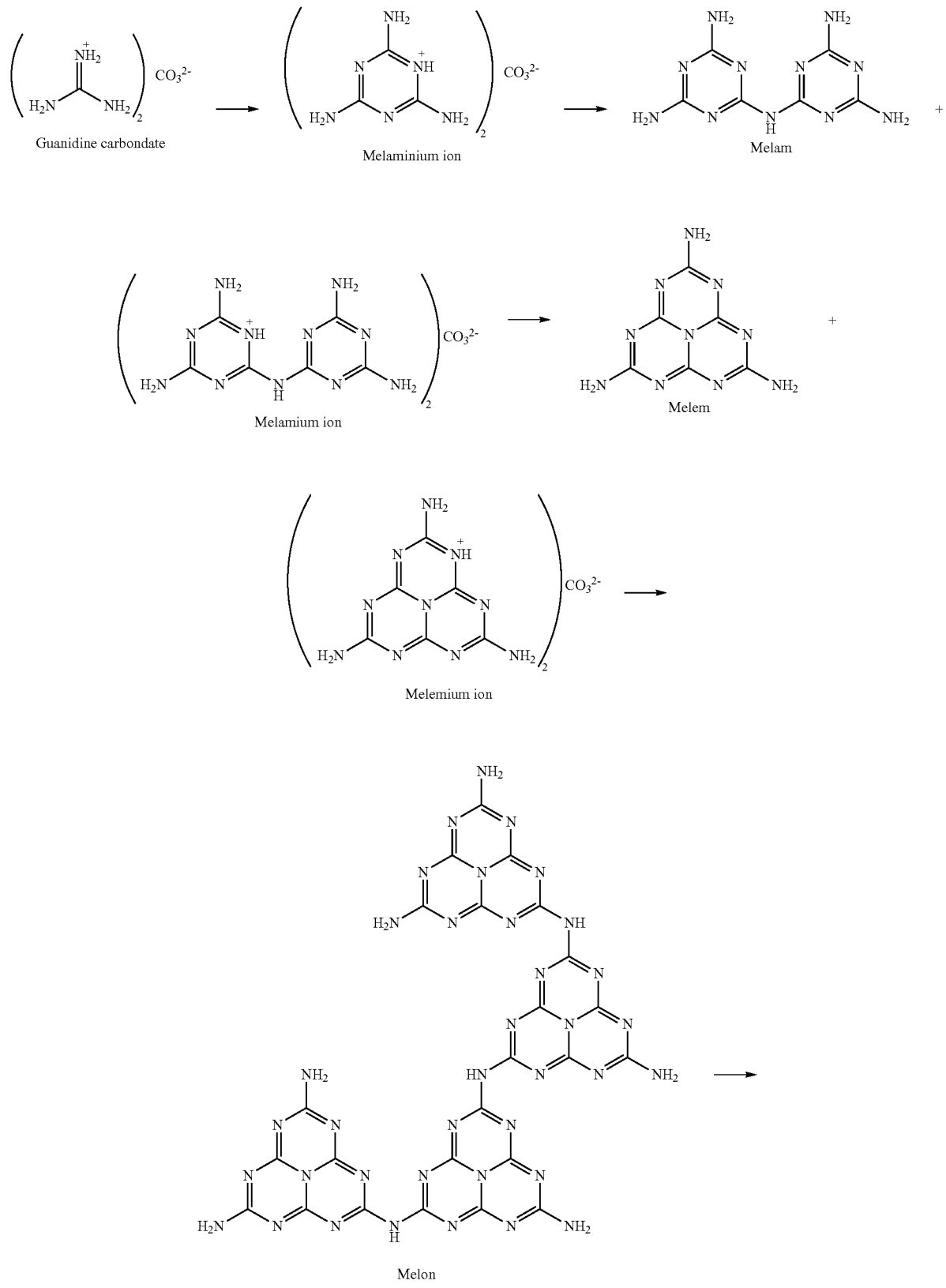

-continued

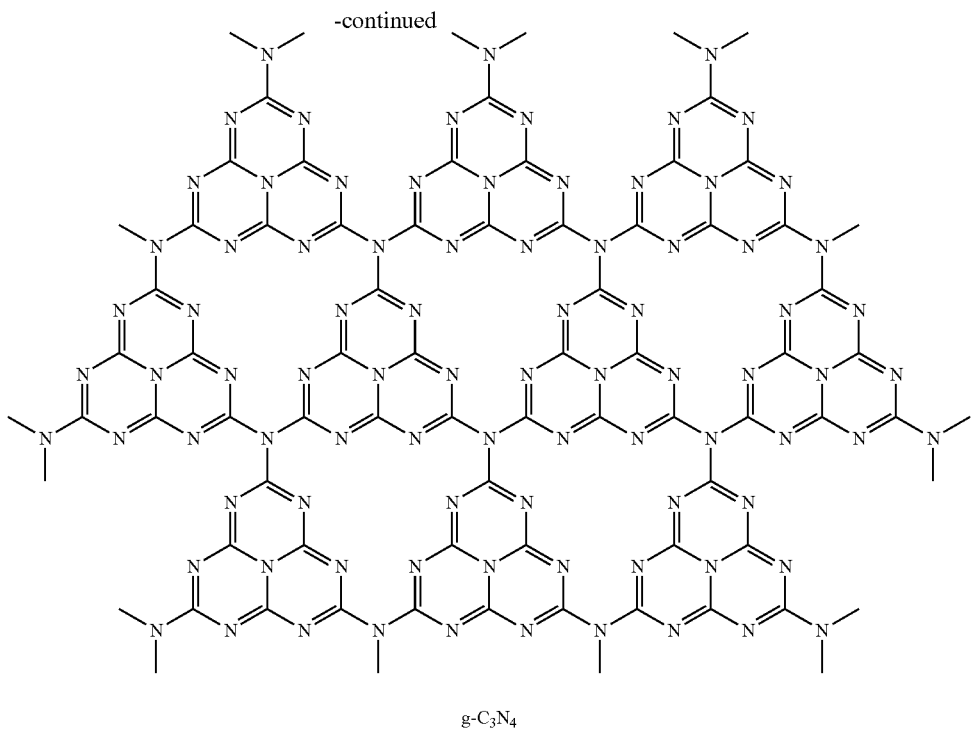

g-C$_3$N$_4$

In the above scheme, a melemium ion obtained through transformations is expected to vaporize (sublime) (see Reference Example described later). Accordingly, in a case where X$^+$ is the one selected from a guanidium ion, a melaminium ion, a melamium ion, a melemium ion, a guanidine derivative ion represented by Formula (I), and a guanidine derivative ion represented by Formula (II), the one that vaporizes and is deposited over the base material is considered as a melemium ion (in salt form) caused by heating.

It should be noted that the term "vaporization" encompasses both a change from a liquid to gas and a direct change (sublimation) from a solid to gas.

The amount of starting material to be used may be determined appropriately according to intended thickness and area of a film to be produced. The heating temperature may be appropriately determined according to the type of starting material to be used. The heating temperature is in a range from, for example, 300° C. to 700° C., and preferably 380° C. to 550° C. The heating time can be set appropriately according to the thickness of a g-C$_3$N$_4$ film to be produced. The heating time can be in a range from, for example, one minute to four hours.

The vaporized starting material or its reactant (referred to as "vaporized substance") is deposited over the surface of the base material having a surface carrying negative electric charges or having π electrons. Since the vaporized substance has positive electric charges as described previously, charge interaction occurs between the vaporized substance and the base material having a surface carrying negative electric charges. Thus, the vaporized substance is deposited over the surface of the base material, the surface carrying negative electric charges. Further, since the vaporized substance has π electrons, the vaporized substance interacts with the base material having a surface having π electrons. Thus, the vaporized material is deposited over the surface of the base material, the surface having π electrons.

In this case, the base material is being heated. Thus, when the vaporized substance is deposited over the surface of the base material, polymerization of the vaporized substance occurs one after another on the base material. This produces g-C$_3$N$_4$. The obtained g-C$_3$N$_4$ is derived from X$^+$ of the compound X$^+_m$Y$^{m-}$. The anion (Y$^{m-}$) is considered to detach through reaction with a proton (H$^+$) of the vaporized substance concurrently with the polymerization reaction into g-C$_3$N$_4$ on the base material (see Reference Example described later). For example, in a case where Y$^{m-}$ is CO$_3^{2-}$, a proton and CO$_3^{2-}$ react with each other. As a result, desorption of CO$_2$ and H$_2$O$_3^2$O occurs. Further, when a layer of g-C$_3$N$_4$ is formed onto the base material, the substance vaporized thereafter is deposited over (adsorbed by) the surface of g-C$_3$N$_4$ through interaction with π electrons of the g-C$_3$N$_4$ thus formed. Then, further polymerization reaction into g-C$_3$N$_4$ on the previously formed g-C$_3$N$_4$ proceeds. In this way, it is possible to produce a film of g-C$_3$N$_4$ on the base material.

The temperature at which the base material is to be heated may be appropriately determined according to the type of starting material to be used. Such a temperature is in a range from, for example, 300° C. to 700° C., and preferably 380° C. to 550° C. A time for heating the base material can be set appropriately according to the thickness of a g-C$_3$N$_4$ film to be produced. The heating time can be in a range from, for example, one minute to four hours.

The starting material and the base material may be separately heated or may be heated together. From the viewpoint of simplicity, it is preferable that the starting material and the base material are heated together in one heating means (e.g. a heating furnace). Moreover, when not only the starting material and the base material but also a space between the starting material and the base material are heated as a whole, polymerization reactions of the starting material into g-C$_3$N$_4$ (reaction of the starting material into the vaporized substance, vaporization, and polymerization of the vaporized substance into $g\text{-}C_3N_4$) occurs sequentially. This makes it possible to produce a $g\text{-}C_3N_4$ film of better quality.

Examples of an atmosphere in which the polymerization reactions of the starting material into $g\text{-}C_3N_4$ (reaction of the starting material into the vaporized substance, vaporization, and polymerization of the vaporized substance into $g\text{-}C_3N_4$) are to be carried out include air, nitrogen, argon, helium, and the like.

Further, by diverting, for example, the existing vapor deposition apparatus for organic EL, it is possible to produce a $g\text{-}C_3N_4$ film having a large area.

[$g\text{-}C_3N_4$ Film and its Applications]

A $g\text{-}C_3N_4$ film produced by the production method of the present invention has a single-layer or multilayer sheet structure (see Experiment Example 4 described later). This sheet structure is a sheet structure in which melem structural units are crosslinked in two-dimensional directions. That is, the $g\text{-}C_3N_4$ film having a single-layer sheet structure is a single-layer sheet having melem structural units spread in two-dimensional directions. The $g\text{-}C_3N_4$ film having a multilayer sheet structure is a laminate of a plurality of sheets each having melem structural units spread in two-dimensional directions. One $g\text{-}C_3N_4$ film may have different number of layers in different locations. The $g\text{-}C_3N_4$ film having different number of layers in different locations has a large surface area and is therefore advantageous when it is used as a catalyst. In a $g\text{-}C_3N_4$ film deposited onto the base material, each individual layer (one layer or a plurality of layers) are laminated so as to be parallel to the base material. Further, a $g\text{-}C_3N_4$ film produced by the production method of the present invention may be partially oxidized and thus doped with oxygen. Still further, a $g\text{-}C_3N_4$ film produced by the production method of the present invention may be such that terminal groups of the $g\text{-}C_3N_4$ film are partially substituted with, for example, an amino group or a cyano group, and that the stoichiometric ratio of carbon and nitrogen is not limited to 3:4.

The $g\text{-}C_3N_4$ film of the present invention can be, for example, 0.3 nm to 1 µm in thickness. The thickness of the $g\text{-}C_3N_4$ film of the present invention can be greater than 1 µm. The production method of the present invention enables easily producing a $g\text{-}C_3N_4$ film having a small thickness (for example, on the order of a nanometer to the order of several micrometer) and a $g\text{-}C_3N_4$ film having a large thickness (for example, on the order of several tens of micrometers to the order of a millimeter). The thickness of the $g\text{-}C_3N_4$ film of the present invention can be appropriately selected according to an intended use of the $g\text{-}C_3N_4$ film.

Further, in using the produced $g\text{-}C_3N_4$ film, the $g\text{-}C_3N_4$ film may be peeled from the base material or may be in such a state that it is deposited onto the base material. Still further, the $g\text{-}C_3N_4$ film peeled off from the base material may be used in such a state that the $g\text{-}C_3N_4$ film is fixed to another base material. In a case where the $g\text{-}C_3N_4$ film is to be peeled from the base material, the $g\text{-}C_3N_4$ film is preferably not smaller than 300 nm in thickness.

Examples of a method of peeling the $g\text{-}C_3N_4$ film from the base material include immersing, in water, the base material having the $g\text{-}C_3N_4$ film formed thereon (see Example 6 described later). The immersion of the base material in water enables easy peeling, thus making it possible to simply obtain a free-standing film. The immersion of the base material in water is particularly effective in a case where the base material is a hydrophilic base material made from, for example, glass, FTO glass, and silicon. The peeled $g\text{-}C_3N_4$ film may be transferred to, for example, graphite, and then dried for use.

Examples of a method of fixing the $g\text{-}C_3N_4$ film peeled from the base material on another base material include forming a polymer film (i.e. another base material) on the $g\text{-}C_3N_4$ film formed on the base material so that the $g\text{-}C_3N_4$ film is transferred onto the polymer film. The polymer film may be formed by applying a polymer solution, which is a starting material for the polymer film, onto the $g\text{-}C_3N_4$ film (see Example 7 described later) or may be formed by applying a monomer onto the $g\text{-}C_3N_4$ film and then subjecting the monomer to, for example, heat or light irradiation for polymerization of the monomer (see Example 8 described later). Immersing, in water, the base material having the $g\text{-}C_3N_4$ film formed thereon and the polymer film formed on the $g\text{-}C_3N_4$ film causes only the base material to be separated from the $g\text{-}C_3N_4$ film. This makes it possible to obtain the $g\text{-}C_3N_4$ film fixed on the polymer film. In a case where the base material is glassy carbon, silicon, or the like material, it is possible to transfer the $g\text{-}C_3N_4$ film onto the polymer film without the need for immersing the base material in water. Furthermore, in a case where a flexible material is selected as a material for the polymer film, an obtained $g\text{-}C_3N_4$ film can be used for a flexible device.

The $g\text{-}C_3N_4$ film of the present invention functions as a photocatalyst. By immersing the $g\text{-}C_3N_4$ film in water and then irradiating the $g\text{-}C_3N_4$ film immersed in water with light, it is possible to produce hydrogen. The $g\text{-}C_3N_4$ film enables simple and easy recovery from the water after use, as compared with the conventional powdery $g\text{-}C_3N_4$. The water may contain an electrolyte and/or a sacrificial reagent as appropriate. The $g\text{-}C_3N_4$ film may also be used in combination with a co-catalyst.

Further, the $g\text{-}C_3N_4$ film of the present invention can be used not only for hydrogen production, but also for degradation of NOx, methylene blue, a volatile organic matter (e.g. acetaldehyde treated as sick house gas), and the like. Still further, the $g\text{-}C_3N_4$ film of the present invention can be used as a catalyst for $CO_2$ reduction or organic synthesis. Yet further, the $g\text{-}C_3N_4$ film of the present invention can be used for $O_2$ reduction (as a fuel cell catalyst, for example).

Further, the $g\text{-}C_3N_4$ film produced by the production method of the present invention is deposited onto the base material. Thus, it is possible to obtain the base material having the $g\text{-}C_3N_4$ film fixed on a surface thereof. Therefore, it is possible to produce hydrogen with use of the base material having the $g\text{-}C_3N_4$ film fixed on the surface thereof. In this case, there is no need to disperse the $g\text{-}C_3N_4$ film in water. This enables simpler and easier recovery of the $g\text{-}C_3N_4$ film after use.

The $g\text{-}C_3N_4$ film produced by the production method of the present invention has a sheet(s) laminated in parallel and can therefore have a high conductivity anisotropy (see Test Example 6 described later). That is, for example, the $g\text{-}C_3N_4$ film disclosed in Non-Patent Literature 7 is found to be random in film orientation because the X-ray diffraction pattern shows not only a diffraction peak derived from the sheet-to-sheet distance but also a diffraction peak derived from a distance between a molecular skeleton and a molecular skeleton. On the contrary, the $g\text{-}C_3N_4$ film of the present invention is such that a peak obtained for the $g\text{-}C_3N_4$ film by out-of-plane X-ray diffraction is derived from a sheet-to-sheet distance only (see Test Example 4 described later). The sheet-to-sheet distance is preferably in a range from 3.17 Å to 3.26 Å. Thus, the $g\text{-}C_3N_4$ film of the present invention can have a higher conductivity anisotropy, as compared with the g-$C_3N_4$ film described in Non-Patent Literature 7. Further, the g-$C_3N_4$ film of the present invention can have transparency.

Still further, the g-$C_3N_4$ film of the present invention can exhibit a high photoconductivity, as compared to the powdery g-$C_3N_4$ produced by the conventional method (see Test Example 6 described later). The photoconductivity of the g-$C_3N_4$ film of the present invention can be, for example, $10^{-5}$ cm$^2$ V$^{-1}$ s$^-$to $10^{-3}$ cm$^2$ V$^{-1}$ s$^{-1}$. A high photoconductivity will prevent deactivation of a carrier. Thus, the g-$C_3N_4$ film of the present invention is suitably used as a photocatalyst and as a solar cell material.

Further, the g-$C_3N_4$ film of the present invention can produce a high photocurrent, as compared to the powdery g-$C_3N_4$ produced by the conventional method (see Test Example 9 described later). The g-$C_3N_4$ film of the present invention can produce a photocurrent of not less than 0.8 µA/cm$^2$ when the g-$C_3N_4$ film is irradiated with visible light of not less than 420 nm while a constant voltage of 0.2 V is applied to the g-$C_3N_4$ film.

Still further, depending on the type of $Y^{m-}$ in the compound $X^+_m Y^{m-}$ used as the starting material, the g-$C_3N_4$ film performs the oxidation (upward) reaction or reduction (downward) reaction (see Test Example 14 described later). Thus, it is possible to easily obtain the g-$C_3N_4$ film that performs reaction in a desired direction, i.e. oxidation (upward) reaction or reduction (downward) reaction, by selecting the type of $Y^{m-}$.

In addition, the g-$C_3N_4$ film of the present invention has a high conductivity anisotropy, as mentioned above, and thus has a fixed transport direction in which a carrier is easier to be flown. Therefore, using the g-$C_3N_4$ film as a semiconductor photoelectrode allows separation of an oxygen-generating site and a hydrogen-generating site. For example, a semiconductor photoelectrode is configured such that a g-$C_3N_4$ film formed on an electrically conductive substrate made from, for example, ITO, FTO, or graphite is a working electrode, silver/silver chloride is a reference electrode, and platinum is a counter electrode, and that the working electrode and the counter electrode are separated from each other by an ion-exchange membrane made from, for example, Nafion. Upon irradiation with light, the g-$C_3N_4$ film generates electrons. The electrons thus generated are moved to the counter electrode, so that hydrogen is produced on the surface of the platinum. Thus, the separation of the working electrode and the counter electrode from each other allows recovery of hydrogen only. Therefore, it is possible to produce hydrogen efficiently.

The conventional water photolysis with use of a powdery g-$C_3N_4$ produces hydrogen and oxygen simultaneously and eventually requires gas separation. In addition, it is known that detonating gas, which is a mixed gas of hydrogen and oxygen, causes explosive reaction by ignition. Therefore, simultaneous production of hydrogen and oxygen arises concerns such as necessity and safety of hydrogen recovery and is a major problem in commercializing photocatalysts. Using the g-$C_3N_4$ film of the present invention allows recovery of hydrogen only and therefore allows solving the above problem.

[Others]

Further, the present invention provides a method for producing g-$C_3N_4$, the method including heating, as a starting material, a compound represented by $X^+_2 CO_3^{2-}$ or $X^+ CH_3COO^-$ to polymerize the compound, thereby generating a graphitic carbon nitride. The definitions of $X^+_2 CO_3^{2-}$ or $X^+ CH_3COO^-$ are as described previously. $X^+$ is preferably a guanidium ion. The g-$C_3N_4$ produced by this production method may be in powder form or may be in film form.

[Conclusion]

As described above, a method for producing a g-$C_3N_4$ film according to the present invention includes the steps of: heating, as a starting material, a compound represented by $X^+_m Y^{m-}$, wherein $X^+$ is selected from a guanidium ion, a melaminium ion, a melamium ion, a melemium ion, a guanidine derivative ion represented by Formula (I) below, and a guanidine derivative ion represented by Formula (II) below, $Y^{m-}$ is an anion, and m is a valence of Y,

[Chem. 7]

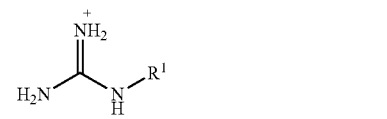

(I)

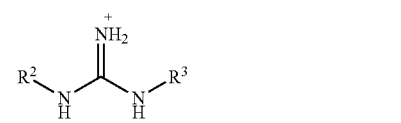

(II)

wherein, in Formulae (I) and (II), $R^1$, $R^2$, and $R^3$ are independently selected from an amino group, a nitro group, an alkyl group having 1 to 10 carbon atoms, —$(C_2H_4O)_n$—$R^4$ (where n is 1 to 10, and $R^4$ is an alkyl group having 1 to 4 carbon atoms), halogen, and a primary amide group, to vaporize the compound or its reactant; and depositing the compound or the reactant over a surface of a base material heated, the surface carrying negative electric charges or having π electrons, so that the compound or the reactant is polymerized on the base material to generate a graphitic carbon nitride.

The production method according to the present invention is preferably such that the constituent $Y^{m-}$ is selected from $CO_3^{2-}$, $SO_4^{2-}$, $Cl^-$, and $R^5COO^-$ where $R^5$ is selected from an alkyl group, an alkenyl group, a halogenated alkyl group, a carboxy group, a carboxyalkyl group each of which has 1 to 10 carbon atoms, and a phenyl group which may be substituted with another group.

The production method according to the present invention is more preferably such that the constituent $Y^{m-}$ is selected from $CO_3^{2-}$ and $CH_3COO^-$.

The production method according to the present invention is preferably such that the constituent $X^+$ is selected from the guanidium ion, the melaminium ion, the melamium ion, and the melemium ion.

The production method according to the present invention is more preferably such that the constituent $X^+$ of the compound is the guanidium ion.

The production method according to the present invention is preferably such that the base material is a substrate which is made from a material selected from glass, quartz glass, indium tin oxide (ITO) glass, fluorine-doped tin oxide (FTO) glass, silicon, graphite, and a glassy carbon.

The production method according to the present invention is preferably such that the compound and the base material are heated at a temperature in a range of 300° C. to 700° C.

Further, the present invention provides a g-$C_3N_4$ film produced by the above production method.

Still further, the present invention provides a base material having the g-$C_3N_4$ film fixed on a surface thereof.

Yet further, the present invention provides an electrically conductive substrate having the g-$C_3N_4$ film fixed on a surface thereof.

Further, the present invention provides a method for producing hydrogen, the method including the steps of immersing the g-$C_3N_4$ film in water; and irradiating the g-$C_3N_4$ film immersed in water with light.

Still further, the present invention provides a method for producing g-$C_3N_4$, the method including the steps of: heating, as a starting material, a compound represented by $X^+_2CO_3^{2-}$ or $X^+CH_3COO^-$, wherein $X^+$ is selected from a guanidium ion, a melaminium ion, a melamium ion, a melemium ion, a guanidine derivative ion represented by Formula (I) above, and a guanidine derivative ion represented by Formula (II) above, to polymerize the compound, thereby generating a graphitic carbon nitride.

The g-$C_3N_4$ production method according to the present invention is preferably such that the constituent $X^+$ is a guanidium ion.

Further, the present invention provides a g-$C_3N_4$ film having a single-layer or multilayer sheet structure.

The sheet structure is preferably a sheet structure in which melem structural units are crosslinked in two-dimensional directions.

Further, the present invention provides a g-$C_3N_4$ film having a sheet structure in which melem structural units are crosslinked in two-dimensional directions, wherein a peak obtained for the g-$C_3N_4$ film by out-of-plane X-ray diffraction is derived from a sheet-to-sheet distance only.

The sheet-to-sheet distance is preferably in a range from 3.17 Å to 3.26 Å.

Further, the present invention provides a g-$C_3N_4$ film that produces a photocurrent of not less than 0.8 $\mu A/cm^2$ when the g-$C_3N_4$ film is irradiated with visible light of not less than 420 nm while a constant voltage of 0.2 V is applied to the g-$C_3N_4$ film.

Still further, the present invention provides a g-$C_3N_4$ film having transparency.

The following will provide Examples to more specifically describe embodiments of the present invention. As a matter of course, the present invention is not limited to Examples provided below, but details of the present invention can be realized in various manners. Further, the invention is not limited to the embodiments described above, and it may be varied in various ways within the scope of the appended Claims. Thus, an embodiment achieved by combining technical means varied appropriately within the scope of the appended claims will be included by the technical scope of the invention. In addition, the present specification encompasses the contents of the specification and/or drawings of Japanese Patent Application No. 2012-280283, to which the present application claims priority. All of the publications, patents, patent applications referred herein are incorporated herein by reference in their entirety.

EXAMPLES

Example 1

Preparation of g-$C_3N_4$ Film

Preparation of g-$C_3N_4$ films was performed with use of an apparatus schematically illustrated in FIG. 1. Guanidine carbonate (3.0 g, 16.7 mmol) was spread all over the bottom of each of Pyrex (registered trademark) test tubes (35 mL), and individual substrates were placed on aluminum foil supports located in the middle of the test tubes. As the substrates, glass, quartz glass, ITO glass, FTO glass, graphite (HOPG substrate), and Si substrates were used. With use of a tubular furnace (KOYO KTF035N1), the temperatures of the test tubes were raised at a rate of 10° C./min, and the test tubes were then heated in air at 550° C. for two hours. After the completion of heating, the test tubes were naturally cooled to room temperature. This yielded yellow films on the individual substrates. With use of the films thus obtained, tests (Test Examples 1 to 10) below were performed.

Test Example 1

Structure Determination of g-$C_3N_4$ Film by X-ray Diffraction Measurement

Figure 2:
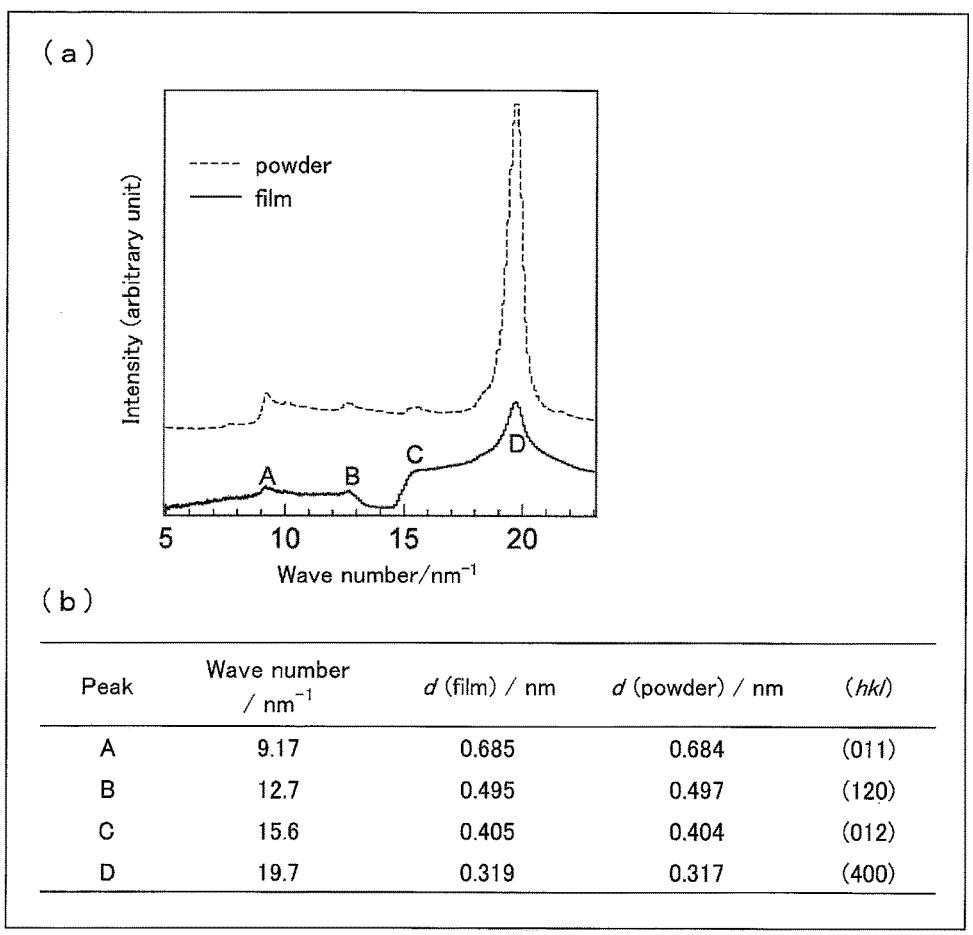
FIG. 2 is a graph showing the result of X-ray diffraction measurement in Test Example 1.

The film prepared on the glass substrate was immersed in pure water for some time, and the film separated from the substrate was then collected. The film thus collected was subjected to X-ray diffraction measurement (apparatus name: BL45XU in SPring-8 with R-AXIS IV++). Similarly, g-$C_3N_4$ powder was subjected to X-ray diffraction measurement for comparison. Note that the g-$C_3N_4$ powder was generated at the bottom of the test tube during the film preparation in Example 1. Obtained X-ray diffraction patterns are shown in (a) of FIG. 2. (b) of FIG. 2 shows attributions of the peaks.

A diffraction pattern corresponding to orthorhombic crystal system (a=12.48516 Å, b=10.90106 Å, c=8.69150 Å) was obtained. For the X-ray diffraction pattern of the film, peaks appeared at the same wavenumbers as those at which peaks of the g-$C_3N_4$ powder appeared.

Test Example 2

Structure Determination of g-$C_3N_4$ Film by IR Spectrum Measurement

Figure 3:
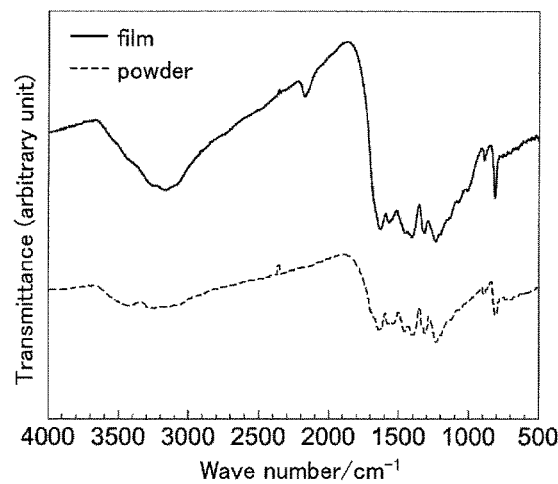
FIG. 3 is a graph showing the result of IR spectrum measurement in Test Example 2.

The film prepared on the glass substrate was immersed in pure water for some time, and the film separated from the substrate was dried at 70° C. for 4 hours and then was used as a sample. The sample thus obtained was subjected to IR spectrum measurement (apparatus name: Fourier transform infrared spectrophotometer, model number: FT/IR-4100). Similarly, IR spectrum of the g-$C_3N_4$ powder was measured for comparison. The IR spectra thus obtained are shown in FIG. 3.

In the IR spectrum of the film, peaks appeared similarly to the peaks of the g-$C_3N_4$ powder. Specifically, a peak characteristic of a triazine skeleton and a heptazine skeleton appeared at 810 $cm^{-1}$, a peak derived from a carbon-nitrogen bond appeared at 1700 to 1000 $cm^{-1}$, and a peak derived from a terminal amino group appeared at 3500 to 3000 $cm^{-1}$. The results of Test Examples 1 and 2 revealed that the film is of the same structure as that of the g-$C_3N_4$ powder.

Test Example 3

Figure 4:
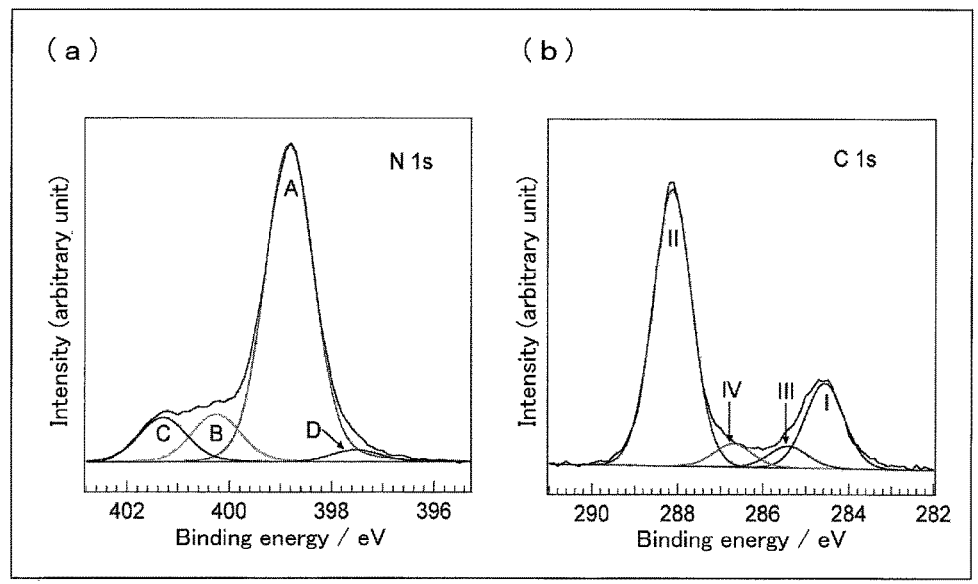
FIG. 4 is a graph showing the result of X-ray photoelectron spectroscopy spectra measurement in Test Example 3.

Structure Determination of g-$C_3N_4$ Film by X-ray Photoelectron Spectroscopy Spectra Measurement X-ray photoelectron spectroscopy spectra of the film formed on n-Si substrate was measured (apparatus name: high-performance X-ray photoelectron spectrometer, model number: ESCALAB 250). X-ray photoelectron spectroscopy spectra are shown in FIG. 4. (a) of FIG. 4 shows the spectrum in range of N 1 s, and (b) of FIG. 4 shows the spectrum in range of C 1 s.

In the spectrum in range of N 1 s, four separate peaks appeared. Peak A corresponds to $sp^2$ nitrogen of a melem skeleton, Peak B corresponds to single bond nitrogen (N—(C)$_3$), Peak C corresponds to nitrogen of unreacted —NH$_2$, and Peak D corresponds to nitrogen of a cyano group formed at the terminal. In the spectrum in range of C 1 s, four separate peaks appeared. Peak I corresponds to $sp^2$ carbon (C—C), Peak II corresponds to $sp^2$ carbon (N—C=N) of melem skeleton, Peak III corresponds to carbon of a melem skeleton bonded to unreacted —NH$_2$, and Peak IV corresponds to carbon of a cyano group. This result demonstrates that the formed g-C$_3$N$_4$ film has a melem skeleton as a structural unit.

Test Example 4

Out-of-Plane X-Ray Diffraction of g-C$_3$N$_4$ Film Formed on Substrate

Figure 5:
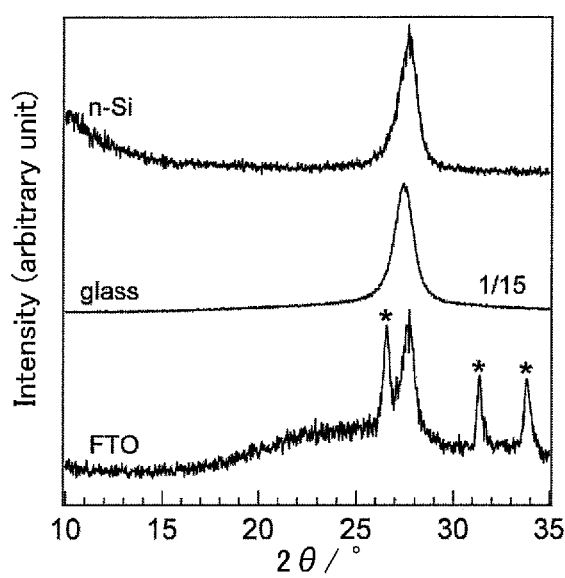
FIG. 5 is a graph showing the result of out-of-plane X-ray diffraction measurement in Test Example 4.

FIG. 5 shows out-of-plane X ray diffraction patterns of the g-C$_3$N$_4$ films formed on the n-Si substrate, the glass substrate, and the FTO glass substrate.

Reflection peak ($2\theta=12.5°$) derived from the inter-melem skeleton could not be observed in the out-of-plane X-ray diffraction. On the other hand, a peak ($2\theta=27.7°$) corresponding to the $\pi$-$\pi$ stack distance (d=0.32 nm) was obtained regardless of the type of substrate. This demonstrates that the $\pi$ stack is overlaid on the substrate so as to be in parallel to the substrate, a two-dimensional sheet of g-C$_3$N$_4$ is formed on the substrates so as to be horizontal to the substrate. Similar results were obtained for the p-Si substrate, the quartz glass substrate, and the graphite substrate, or equivalently, parallel orientation with respect to the substrate was always achieved.

Test Example 5

Observation of g-C$_3$N$_4$ Film Under Scanning Electron Microscope

Figure 6:
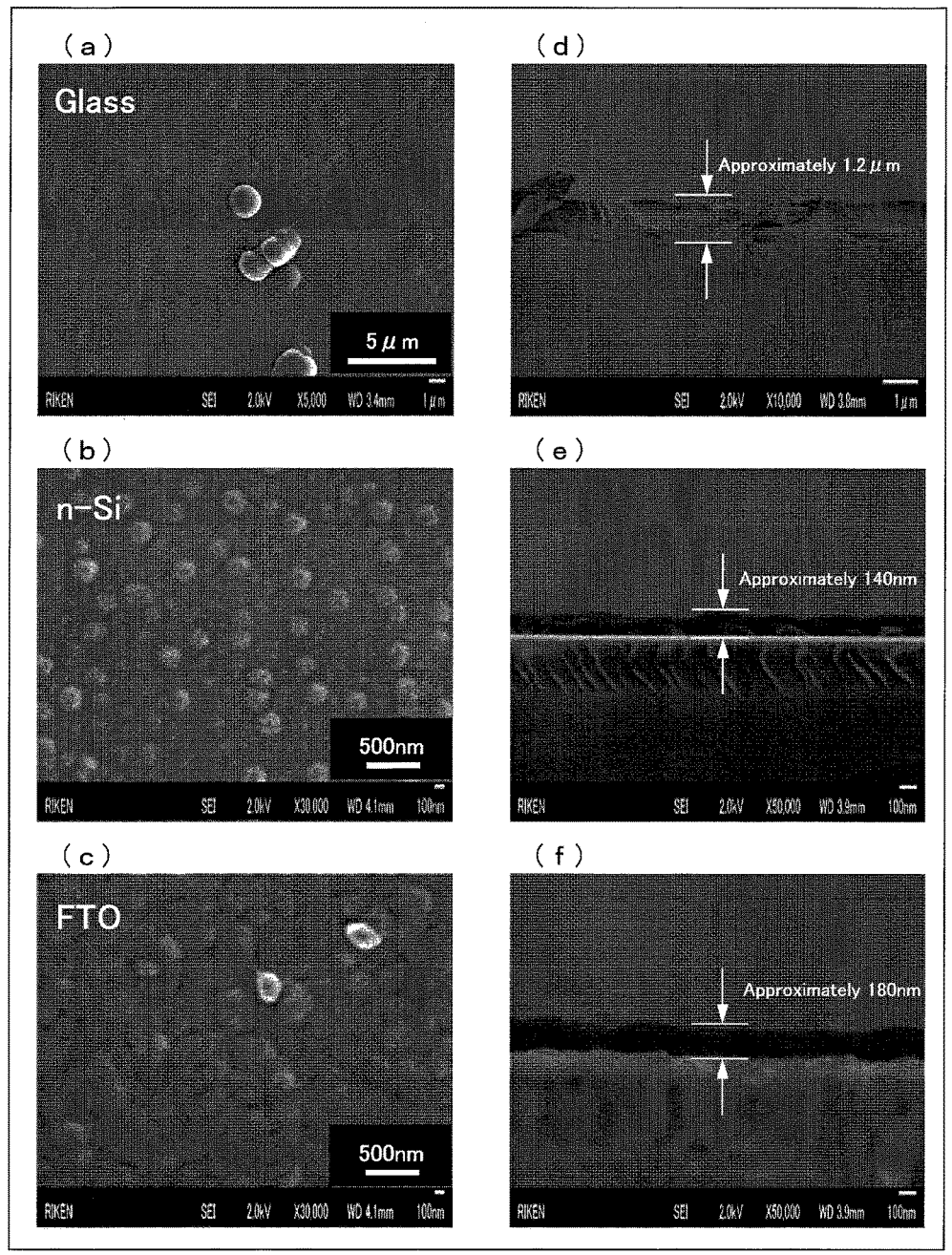
FIG. 6 is a view showing an observation image obtained by scanning electron microscopic observation in Test Example 5.

Observations of the g-C$_3$N$_4$ films formed on the substrates were performed using a scanning electron microscope (device name: field emission electron microscope, model number: JSM-6330F). FIG. 6 shows surface observation images of the g-C$_3$N$_4$ films and cross-sectional observation images of the g-C$_3$N$_4$ films ((a) glass substrate (surface), (b) n-Si substrate (surface), (c) FTO glass substrate (surface), (d) glass substrate (cross section), (e) n-Si substrate (cross section), and (f) FTO glass substrate (cross-section)).

Surface observations determined that a domain of 100 nm to 400 nm in size was formed on the n-Si substrate and the FTO glass substrate, while a domain of 1 μm to 2 μm in size was formed on the glass substrate. On the basis of this result, together with the results of X-ray diffraction, it can be concluded that the g-C$_3$N$_4$ sheet is formed in the domain. In addition, cross-section observations determined that a film of 100 nm to 200 nm in thickness was formed on the n-Si substrate and the FTO glass substrate, while a film of about 1 μm in thickness was formed on the glass substrate. Domain formation makes the g-C$_3$N$_4$ film advantageous, for use as a photocatalyst, in increasing a surface area.

Test Example 6

Photoconductivity of g-C$_3$N$_4$ Film

Figure 7:
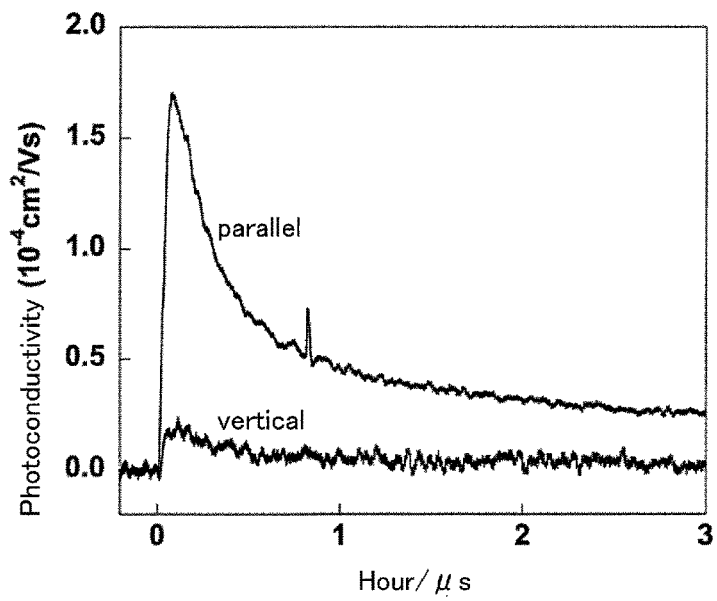
FIG. 7 is a graph showing the result of optical excitation time-resolved microwave conductivity measurement in Test Example 6.

The film on the glass substrate was immersed in pure water for two days so as to be slowly separated from the glass substrate. Then, the film thus separated was transferred onto a quartz glass substrate to prepare a sample. Photoconductivity of the film was examined through flash photolysis time-resolved microwave conductivity measurement (device name: photoexcitation, time-resolved microwave conductivity device). The measurement was carried out under the condition that excitation wavelength was 420 nm, and excitation light intensity was $5.4\times10^{15}$ photons cm$^{-2}$pulse$^{-1}$. The measurement results are shown in FIG. 7.

Photoconductivity of g-C$_3$N$_4$ film was more than twice greater than that of the g-C$_3$N$_4$ powder. Further, photoconductivity in a direction parallel to the substrate was 9.8 times greater than that in a direction vertical to the substrate. From this result, it is considered that the photoconductivity in the parallel direction is a high conductivity ($1.64\times10^{-4}$ cm$^2$ V$^{-1}$s$^{-1}$) because the g-C$_3$N$_4$ sheet is spread in parallel to the substrate. A high photoconductivity makes the g-C$_3$N$_4$ film advantageous for use as a photocatalyst and a solar cell material in that it prevents deactivation of a carrier.

Test Example 7

Diffuse Reflectance Spectrum of g-C$_3$N$_4$ Film

Figure 8:
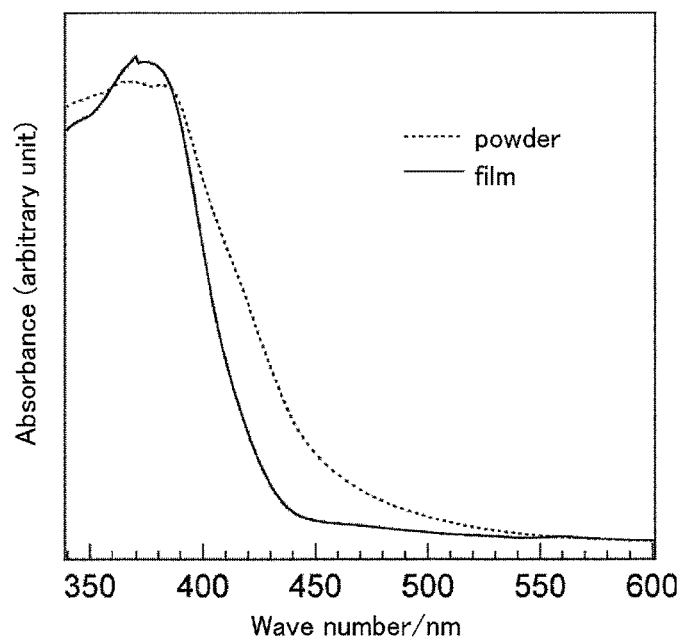
FIG. 8 is a graph showing the result of diffuse reflectance spectrum measurement in Test Example 7.

The film prepared on the n-Si substrate was immersed in pure water, and the film separated from the n-Si substrate was then collected. The film thus collected was subjected to diffuse reflectance spectrum measurement (apparatus names: UV-visible-near infrared spectrophotometer and integrating sphere unit, model numbers: V-670 and ISN-723). Similarly, diffuse reflectance spectrum of the g-C$_3$N$_4$ powder was measured for comparison. Obtained diffuse reflectance spectra are shown in FIG. 8.

Optical gaps of the g-C$_3$N$_4$ film and the g-C$_3$N$_4$ powder were 2.85 eV and 2.72 eV, respectively. It was found that the optical gap of the g-C$_3$N$_4$ film is greater than that of the g-C$_3$N$_4$ powder.

Test Example 8

Identification of Energy Level of g-C$_3$N$_4$ Film

Figure 9:
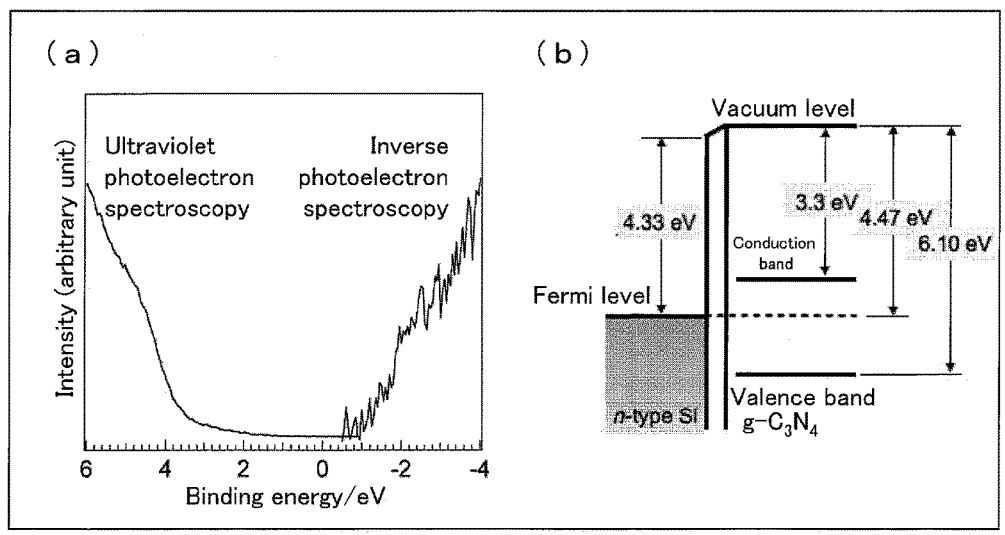
FIG. 9 is a diagram showing energy level evaluations in Test Example 8.

Electronic properties of the g-C$_3$N$_4$ film prepared on the n-Si substrate were evaluated under ultraviolet photoelectron spectrum measurement and inverse photoelectron spectrum measurement (device name: ultraviolet photoelectron spectrometer, model number: EA125). (a) of FIG. 9 shows an ultraviolet photoelectron spectrum and an inverse photoelectron spectrum. (b) of FIG. 9 shows an energy diagram of the g-C$_3$N$_4$ film.

In the ultraviolet photoelectron spectrum, a shoulder was observed at about 4.7 eV. In the inverse photoelectron spectrum, a shoulder was observed at about −2.0 eV. These shoulders can be attributed to energy level derived from the $\pi$ orbit of g-C$_3$N$_4$ spread two-dimensionally. In addition, in the ultraviolet photoelectron spectroscopy spectrum, a hem of the spectrum was observed on the low binding energy side, whereas a rise of the spectrum was determined to be 1.63 eV. On the other hand, a rise of the inverse photoelectroscopy spectrum was −1.2 eV. From a rise of a secondary electron region, Fermi level was determined to be 4.47 eV, and ionization potential, electron affinity, and band gap were 6.10 eV, 3.3 eV, and 2.8 eV, respectively. The ionization potential of the powder was determined to be 6.10 eV by photoelectron spectroscopy measurement in an atmosphere. Good agreement with the result for the film was observed. Further, the band gap determined from photoelectron spectroscopy corresponded well with the optical gap obtained from the diffuse reflectance spectrum.

Moreover, the conduction band (−3.3 eV) of the $g$-$C_3N_4$ film had a higher reducing power than the reduction potential of proton (−4.44 eV under vacuum). Thus, the $g$-$C_3N_4$ film was confirmed to satisfy the conditions for a catalyst for hydrogen generation through water photolysis.

Test Example 9

Photoresponsivity of $g$-$C_3N_4$ Film

Figure 10:
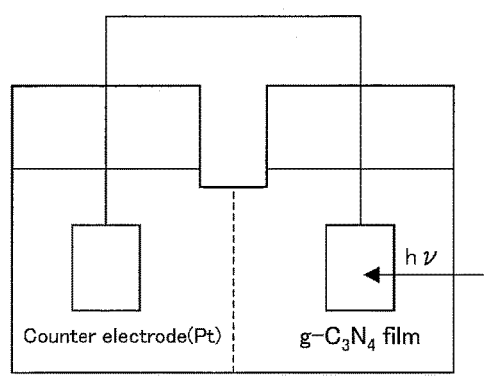
FIG. 10 is a schematic diagram illustrating an optical electrode cell used in Test Example 9.
Figure 11:
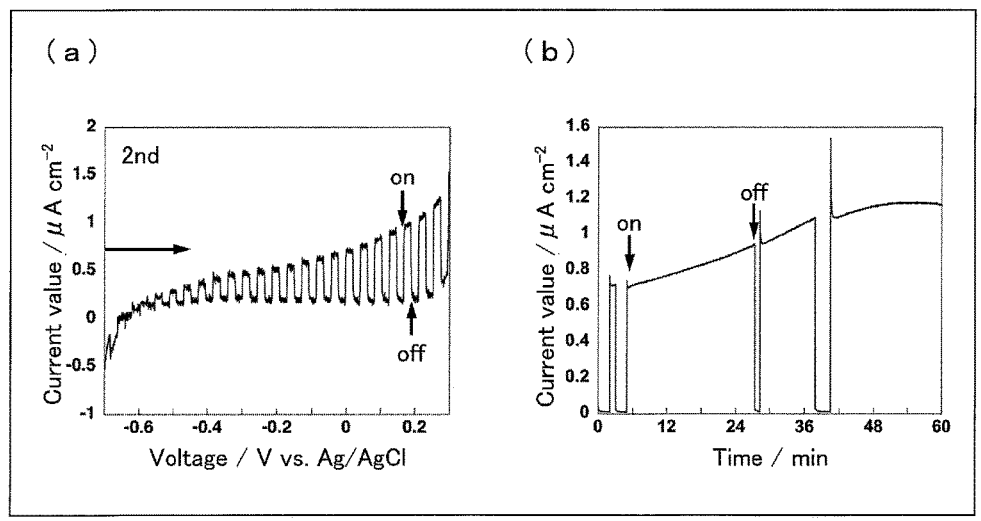
FIG. 11 is a graph showing the result of photoresponsivity in Test Example 9.

Photoresponsivity of the $g$-$C_3N_4$ film was evaluated with use of an optical electrode cell schematically illustrated in FIG. 10. The $g$-$C_3N_4$ film (size: 20 mm×20 mm) was formed onto a FTO glass substrate and used for the measurement. Platinum (Pt) was used as a counter electrode, 0.1M sodium sulfate was used as an electrolyte, an aqueous solution of 0.025M potassium hydrogenphosphate and 0.025 M sodium hydrogenphosphate was used as a pH buffer. The $g$-$C_3N_4$ film and the counter electrode are isolated from each other by an ion exchange membrane. As a light source, a 300W xenon lamp was used for irradiation of visible light of longer than 420 nm. In addition, a voltage was swept in a range of −0.7 V to 0.3V (sweeping rate: 20 mV/s), and a photocurrent was measured. Further, while application of a constant voltage (0.2 V) was performed, visible light of longer than 420 nm was applied. The result is shown in FIG. 11. (a) of FIG. 11 shows current-voltage characteristic of the $g$-$C_3N_4$ film. (b) of FIG. 11 shows photocurrent stability at 0.2 V.

For the $g$-$C_3N_4$ film, a photocurrent was detected under visible light without using a sacrificial reagent. When the $g$-$C_3N_4$ film was irradiated with light, a current value increased immediately. When the $g$-$C_3N_4$ film was cut off from light, the current value returned to its original value. Moreover, the current value was not decreased even when the $g$-$C_3N_4$ film was irradiated with light for more than 1 hour. Thus, the $g$-$C_3N_4$ film was found to be stable to light. A material having a high photostability is advantageous for use as a photocatalyst and a solar cell.

When the $g$-$C_3N_4$ film was irradiated with visible light of longer than 420 nm while a constant voltage (0.2 V) was applied to the $g$-$C_3N_4$ film, a photocurrent of approximately 1 μA/cm$^2$ was observed. Meanwhile, Wang et al. has confirmed photoresponsivity of a sample obtained by applying $g$-$C_3N_4$ powder onto the ITO glass substrate (reference literature: Angew. Chem. Int. Ed. 2010, 49, 3356-3359). In the experiment conducted by Wang et al., sodium sulfate was used as an electrolyte, and a current value under application of a constant voltage (0.3 V) was approximately 0.14 μA/cm$^2$. This revealed that the $g$-$C_3N_4$ film produces a photocurrent higher than that from the $g$-$C_3N_4$ powder.

Test Example 10

Hydrogen Generation Behavior

Hydrogen generation behaviors of the $g$-$C_3N_4$ film formed on the glass substrate and the $g$-$C_3N_4$ film formed on the p-Si substrate were examined. When the $g$-$C_3N_4$ films were irradiated in water with light from a xenon lamp (>420 nm) while 10 vol % triethanolamine was used as a hole sacrificial reagent, and 0.5 wt % Pt was used as a co-catalyst, bubbles were generated over the surfaces of the films. On examination by gas chromatography, the generated gas was found to be hydrogen. The amounts of hydrogen generated from the $g$-$C_3N_4$ irradiated with light for six hours were 0.023 μmol for the glass substrate and 0.017 μmol for the p-Si substrate.

Example 2

Preparation of $g$-$C_3N_4$ Film

Guanidine sulfate (3.0 g) was placed in a Pyrex (registered trademark) test tube (35 mL). With use of a tubular furnace (KOYO KTF035N1), the temperature of the test tube was raised at a rate of 10° C./min, and the test tube was then heated in air at 550° C. for two hours. After the completion of heating, the test tube was naturally cooled to room temperature. As a result, a product which was partially in film form was observed in the inner wall of the test tube.

Example 3

Preparation of $g$-$C_3N_4$ Film

Guanidine hydrochloride (3.0 g) was placed in a Pyrex (registered trademark) test tube (35 mL). With use of a tubular furnace (KOYO KTF035N1), the temperature of the test tube was raised at a rate of 10° C./min, and the test tube was then heated in air at 550° C. for two hours. After the completion of heating, the test tube was naturally cooled to room temperature. As a result, a product which was partially in film form was observed in the inner wall of the test tube.

Reference Example 1

Thermogravimetry/Differential Thermal Analysis (TG-DTA)

Thermogravimetry/differential thermal analysis (SII Nanotechnology Inc. EXSTAR TG/DTA7300) was performed to determine a reaction behavior of guanidine carbonate with a temperature change. The measurement was performed in the atmosphere at a temperature rise rate of 10° C./min.

As a result of the measurement, a large weight loss of 54.3% was obtained at 192° C., and a large endothermic peak was obtained at 199° C. A weight loss of 32.6% at 283° C. and an endothermic peak at 307° C. were observed. Weight losses occurred at 403° C. and 520° C., and a weight loss of 100% was observed at 570° C. Further, a small endothermic peak appeared at 418° C., and an exothermic peak appeared at 451° C. Then, each guanidine carbonate was heated at temperatures ((a) 230° C., (b) 330° C., (c) 380° C., (d) 430° C., (e) 490° C., (f) 550° C., and (g) 650° C.) and subjected to X-ray photoelectron spectroscopy, X-ray diffraction pattern measurement, and IR measurement.

Reference Example 2

Synthesis

Guanidine carbonate (3.0 g, 16.7 mmol) was placed in a Pyrex (registered trademark) test tube (35 mL), and the test tube was then placed in a tubular furnace (KOYO KTF035N1). In the air, temperatures of the test tubes were raised at a temperature rise rate of 10° C./min to the temperatures ((a) 230° C., (b) 330° C., (c) 380° C., (d) 430° C., (e) 490° C., (f) 550° C., and (g) 650° C.). Thereafter, the test tubes corresponding to the temperatures (a), (b), (c), and (g) were heated for 10 minutes, and the other test tubes corresponding to the temperatures (d), (e), and (f) were heated for 2 hours. The test tubes were naturally cooled to room temperature, and samples remained at the bottoms of the test tubes were then collected.

Reference Example 3

IR Spectra Measurement

Measurement of IR spectra (JASCO FT/IR-4100) was performed to determine structures of the compounds obtained at the temperatures (a) to (g).

As a result of the IR spectra measurement, peaks characteristic of s-triazine skeleton (810 cm$^{-1}$, 1000 cm$^{-1}$ to 1700 cm$^{-1}$) appeared at 230° C. and 330° C. A peak characteristic of s-heptazine skeleton (810 cm$^{-1}$, 1000 cm$^{-1}$ to 1700 cm$^{-1}$) appeared at 380° C. Peaks characteristic of melon (linear melem) skeleton (810 cm$^{-1}$, 1000 cm$^{-1}$ to 1700 cm$^{-1}$) appeared at 430° C. and 490° C. Peaks characteristic of g-$C_3N_4$ (810 cm$^{-1}$, 1000 cm$^{-1}$ to 1700 cm$^{-1}$) appeared at 550° C. and 650° C. The existence of counter anion ($CO_3^{2-}$) was not identified.

Reference Example 4

Diffuse Reflectance Spectra

Measurement of diffuse reflectance spectra (JASCO V-670, JASCO ISN-723) was performed to determine photochemical properties of the compounds obtained at the temperatures (a) to (g).

The diffuse reflectance spectra measurements determined that the compounds obtained at 230° C. and 330° C. were white powders, the compound obtained at 380° C. was slightly yellowish powder, the compounds obtained at 430° C. and 490° C. were yellow powders, the compound obtained at 550° C. was slightly dusty yellow powder, and the compound obtained at 650° C. was reddish powder. As compared to the reflectance spectrum of the compound obtained at 230° C., the reflectance spectrum of the compound obtained at 330° C. shifts to the long wavelength side, and the compound obtained at 330° C. is found to have an s-triazine skeleton by the IR measurement. From this, it was presumed that the compound obtained at 330° C. is of a structure partially similar to melam. In addition, for the compound obtained by heating at 650° C., a new absorption appeared at around 500 nm.

Reference Example 5

X-Ray Diffraction Measurement

X-ray diffraction measurement was performed to determine the structures of the compounds obtained at the temperatures (a) to (g).

As a result, X-ray diffraction patterns of the compounds obtained by heating at 550° C. and 650° C. coincided with the X-ray diffraction pattern obtained for g-$C_3N_4$ synthesized from other monomer. That is, the sample obtained by heating at a temperature of not lower than 550° C. was found to be g-$C_3N_4$. Further, the compounds obtained at 430° C. and 490° C. were found to be melon. This is because peaks appearing at around 19.8 nm$^{-1}$, which peaks derived from a sheet-to-sheet distance, were shifted to a slightly smaller angle side than the peaks appearing for the compounds obtained at 550° C. and 650° C.

Reference Example 6

X-Ray Photoelectron Spectroscopy Spectra

Measurement of X-ray photoelectron spectroscopy spectra (Thermo Scientific K.K. ESCALAB 250, energy resolution of less than 0.45 eV FWHM) was performed to determine behaviors of a proton and a counter anion.

From the result of the measurement of C1s and O1s spectra, it was found that carbonates, which are counter anions, existed in the compounds obtained at 230° C., 330° C., and 380° C. O atoms contained in the compound obtained at 430° C. were different in bond energy from those contained the counter anion, and were therefore considered as $CO_2$ incorporated into the compound.

From the result of the measurement of N1s spectra, the compounds obtained at 230° C. and 330° C. were found to each have an s-triazine skeleton in which an N atom was protonated, and the compound obtained at 380° C. was found to have an s-heptazine skeleton in which an N atom was protonated.

For the compound obtained by heating at a temperature of not lower than 430° C., neither a peak corresponding to the protonated N atom nor a peak corresponding to the O atom derived from the counter anion was obtained. Thus, it is considered that the O atoms were desorbed as $CO_2$ and $H_2O$ from the inside of a polymer concurrently with the polymerization.

Reference Example 7

Mechanism of g-$C_3N_4$ Film Formation

From the results obtained in Reference Examples 1 to 6, a synthetic route of g-$C_3N_4$ formed from guanidine carbonate was presumed as below.

[Chem. 8]

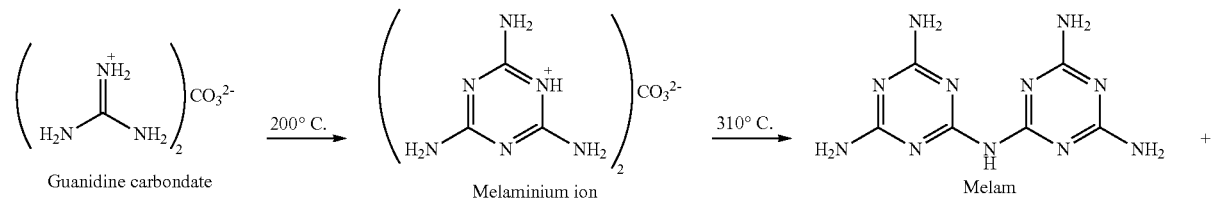

Guanidine carbondate  Melaminium ion  Melam

-continued
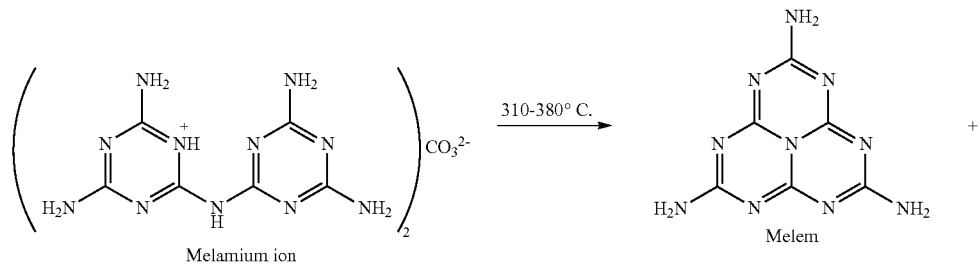
Melamium ion → Melem
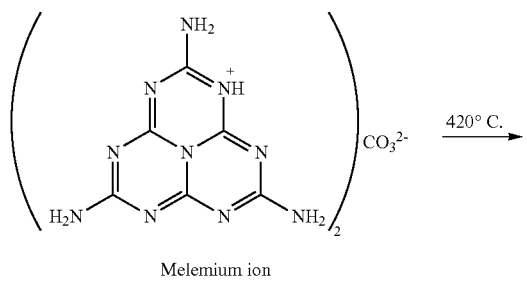
Melemium ion
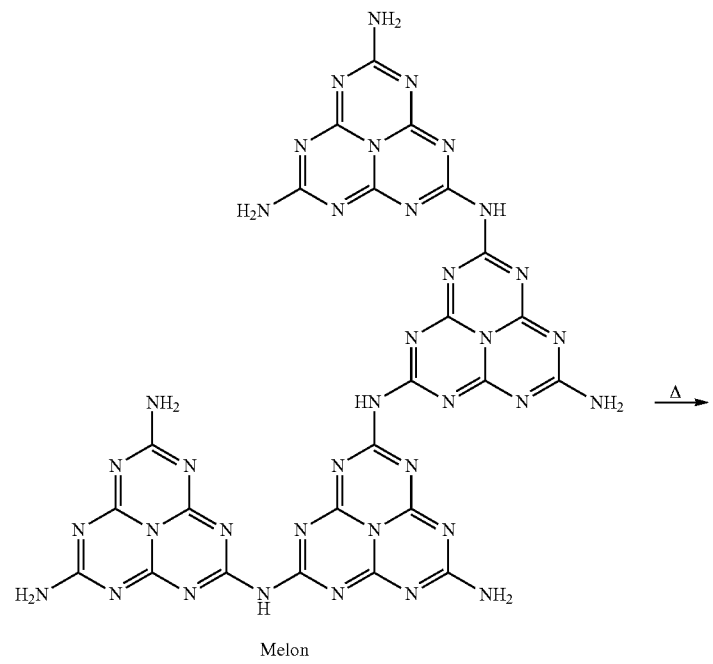
Melon -continued

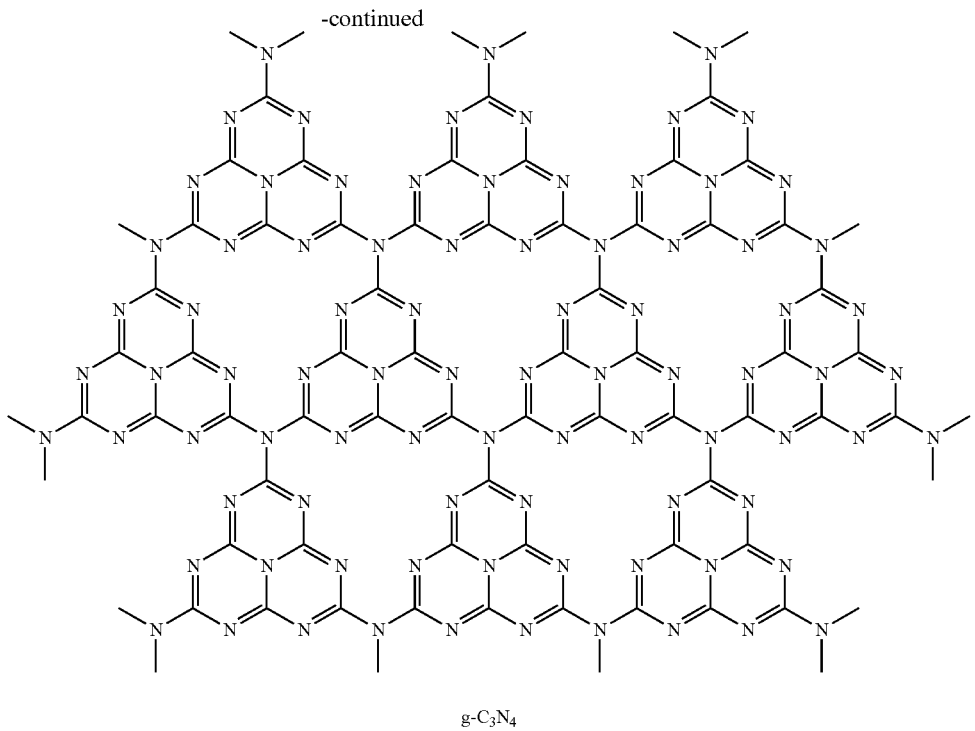

g-C$_3$N$_4$

When the test tube was heated at 430° C., light emission derived from melon was obtained in the test tube. Thus, it was found that a film is formed on the substrate at temperatures in the range from 380° C. to 430° C.

In addition, from the fact that the DTA of Reference Example 1 obtained the endothermic peak at 418° C., it was presumed that sublimation and polymerization of a melemium ion takes place at 418° C. Actually, when the test tube was heated at 420° C., a film was formed on the substrate, and light emission derived from melon was obtained.

No film was formed when the same operation was performed with the starting material replaced by dicyandiamide, urea, thiourea, or the like. Therefore, it was presumed that cationic property of a melemium ion is important for the film formation. The sublimated melemium ion is adsorbed on the surface of a glass substrate by electric charge interactions. As the temperature rises, polymerization proceeds on the substrate, and a proton on a skeleton and a carbonate, which is a counter anion, are desorbed as $CO_2$ and $H_2O$ simultaneously. Further, it was considered that once a g-C$_3$N$_4$ layer was formed on the substrate, subsequently sublimated melemium ions are adsorbed in the same manner by interactions with π electrons of a g-C$_3$N$_4$ sheet, so that g-C$_3$N$_4$ sheets are laminated.

Example 4

Preparation of g-C$_3$N$_4$ Film in Atmosphere of Nitrogen

Figure 12:
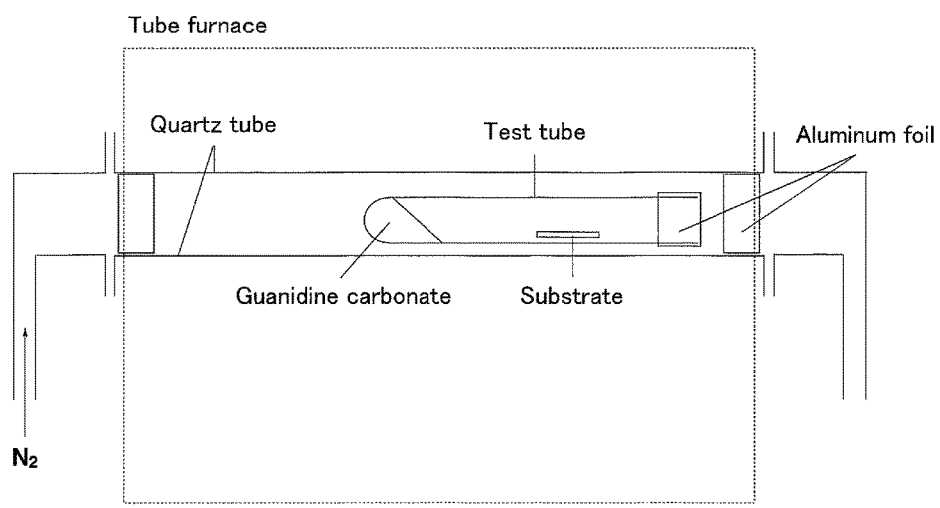
FIG. 12 is a schematic view illustrating an apparatus used in Example 4.

Preparation of g-C$_3$N$_4$ films was performed with use of an apparatus schematically illustrated in FIG. 12. Guanidine carbonate (3.0 g, 16.7 mmol) was spread all over the bottom of each of Pyrex (registered trademark) test tubes (35 mL), individual substrates were placed in the middle of the test tubes. Subsequently, the test tubes were sealed with aluminum foils. As the substrates, glass, FTO glass, and graphite substrate (HOPG substrate) were used. Each of the test tubes was allowed to stand in a quartz tube. With use of a tubular furnace into which nitrogen gas was flown, the temperatures of the test tubes were raised at a rate of 10° C./min, and the test tubes were then heated at 550° C. for two hours. After the completion of heating, the test tubes were naturally cooled to room temperature. This yielded films on the individual substrates. With use of the films thus obtained, tests (Test Examples 11 and 12) below were performed. Note that g-C$_3$N$_4$ powder was produced at the bottom of the test tube.

Test Example 11

Structure Determination of g-C$_3$N$_4$ Film by IR Spectrum Measurement

Figure 13:
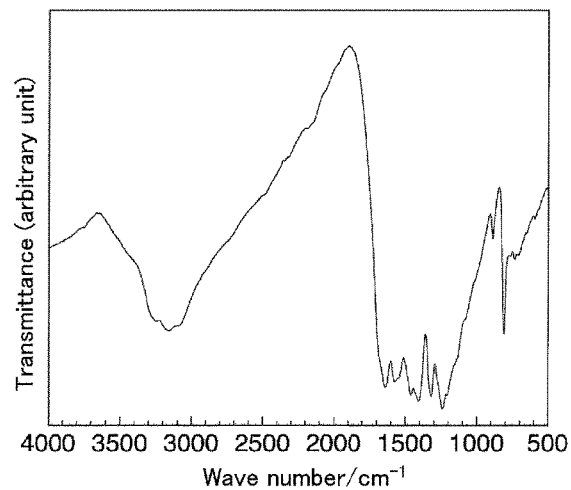
FIG. 13 is a graph showing the result of IR spectrum measurement in Test Example 11.

The film prepared on the FTO glass substrate and peeled off with a spatula was used as a sample. The sample thus obtained was subjected to IR spectrum measurement. The IR spectrum thus obtained is shown in FIG. 13.

In the IR spectrum, peaks appeared similarly to the peaks of the g-C$_3$N$_4$ powder. Specifically, a peak characteristic of a triazine skeleton and a heptazine skeleton appeared at 810 cm$^{-1}$, a peak derived from a carbon-nitrogen bond appeared at 1700 to 1000 cm$^{-1}$, and a peak derived from a terminal amino group appeared at 3500 to 3000 cm$^{-1}$. This result revealed that the film is of the same structure as that of the g-C$_3$N$_4$ powder.

Test Example 12

Figure 14:
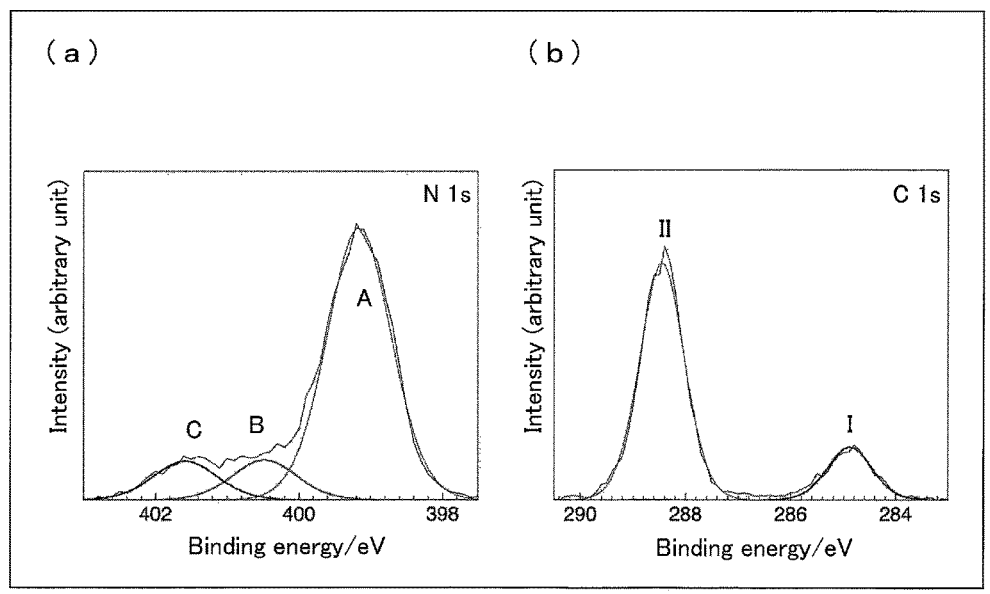
FIG. 14 is a graph showing the result of X-ray photoelectron spectroscopy spectra measurement in Test Example 12.

Structure Determination of g-C$_3$N$_4$ Film by X-Ray Photoelectron Spectroscopy Spectra Measurement X-ray photoelectron spectroscopy spectra of the film formed on the FTO glass substrate were measured. X-ray photoelectron spectroscopy spectra are shown in FIG. 14. (a) of FIG. 14 shows the spectrum in range of N 1 s, and (b) of FIG. 14 shows the spectrum in range of C 1 s.

In the spectrum in range of N 1 s, three separate peaks appeared. Peak A corresponds to $sp^2$ nitrogen of a melem skeleton, Peak B corresponds to single bond nitrogen (N—(C)3), and Peak C corresponds to nitrogen of unreacted —$NH_2$. In the spectrum in range of C 1 s, two separate peaks appeared. Peak I corresponds to $sp^2$ carbon (C—C), and Peak II corresponds to $sp^2$ carbon (N—C=N) of a melem skeleton. This result demonstrates that the formed g-$C_3N_4$ film has a melem skeleton as a structural unit.

Example 5

Preparation of g-$C_3N_4$ Film

Guanidine acetate (0.5 g, 4.2 mmol) was spread all over the bottom of each of Pyrex (registered trademark) test tubes (35 mL), and individual substrates were placed on aluminum foil supports located in the middle of the test tubes (see FIG. 1). As the substrates, glass, graphite, and Si substrates were used. With use of a tubular furnace (KOYO KTF035N1), the temperatures of the test tubes were raised at a rate of 10° C./min, and the test tubes were then heated in air at 550° C. for two hours. After the completion of heating, the test tubes were naturally cooled to room temperature. This yielded red films on the individual substrates. With use of the films thus obtained, a test (Test Example 13) below was performed.

Test Example 13

Figure 15:
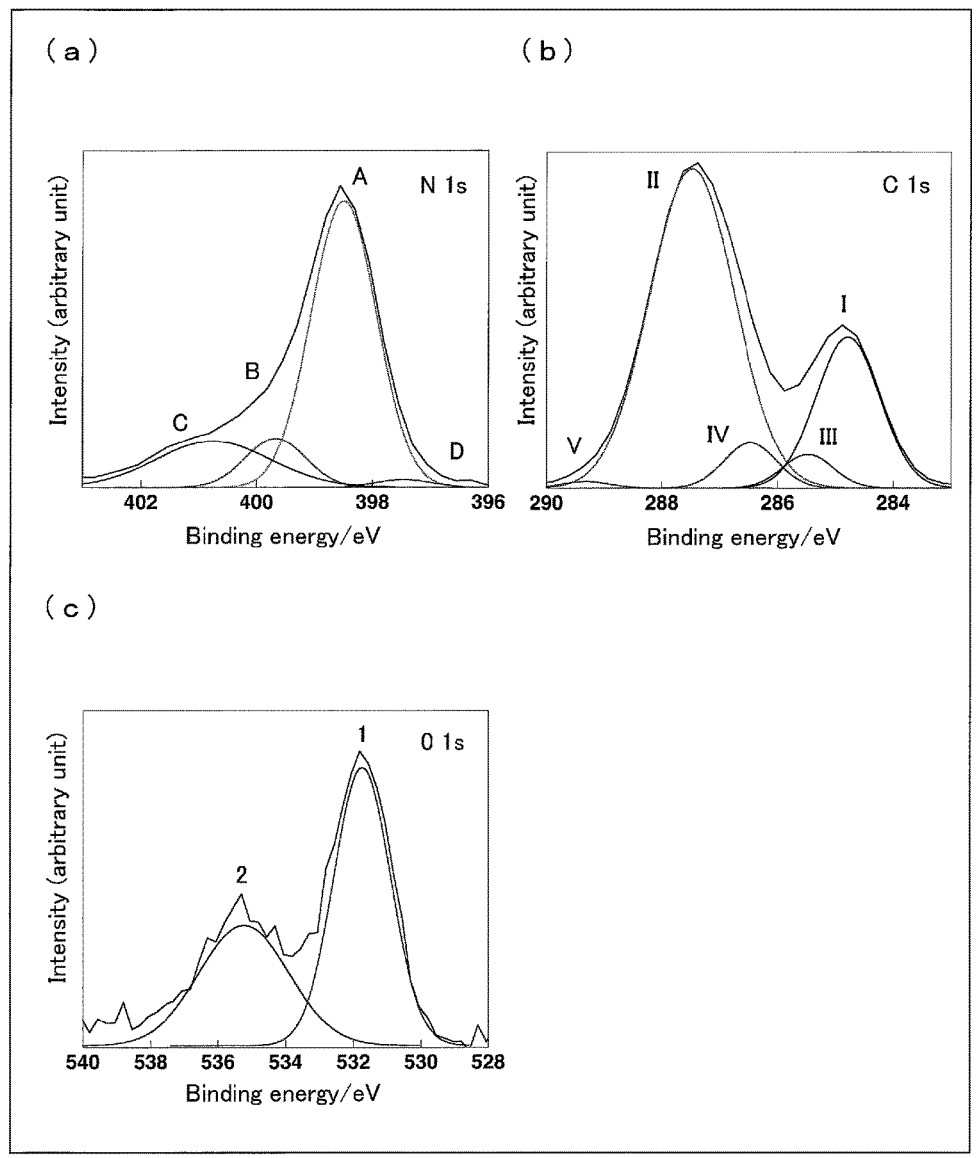
FIG. 15 is a graph showing the result of X-ray photoelectron spectroscopy spectra measurement in Test Example 13.

Structure Determination of g-$C_3N_4$ Film by X-Ray Photoelectron Spectroscopy Spectra Measurement and IR Spectrum Measurement X-ray photoelectron spectroscopy spectra of the film formed on the n-Si substrate were measured. X-ray photoelectron spectroscopy spectra are shown in FIG. 15. (a) of FIG. 15 shows the spectrum in range of N 1 s, (b) of FIG. 15 shows the spectrum in range of C 1 s, and (c) of FIG. 15 shows the spectrum in range of O 1 s.

In the spectrum in range of N 1 s, four separate peaks appeared. Peak A corresponds to $sp^2$ nitrogen of a melem skeleton, Peak B corresponds to single bond nitrogen (N—$(C)_3$), Peak C corresponds to nitrogen of unreacted —$NH_2$, and Peak D corresponds to nitrogen of a cyano group formed at the terminal. In the spectrum in range of C 1 s, four separate peaks appeared. Peak I corresponds to $sp^2$ carbon (C—C), Peak II corresponds to $sp^2$ carbon (N—C=N) of a melem skeleton, Peak III corresponds to carbon of a melem skeleton bonded to unreacted —$NH_2$, Peak IV corresponds to carbon of a cyano group, and Peak V corresponds to carbon of C—O. In the spectrum in range of O 1 s, two separate peaks appeared. Peak 1 corresponds to oxygen of N—C—O, and Peak 2 corresponds to an oxygen molecule adsorbed.

Figure 16:
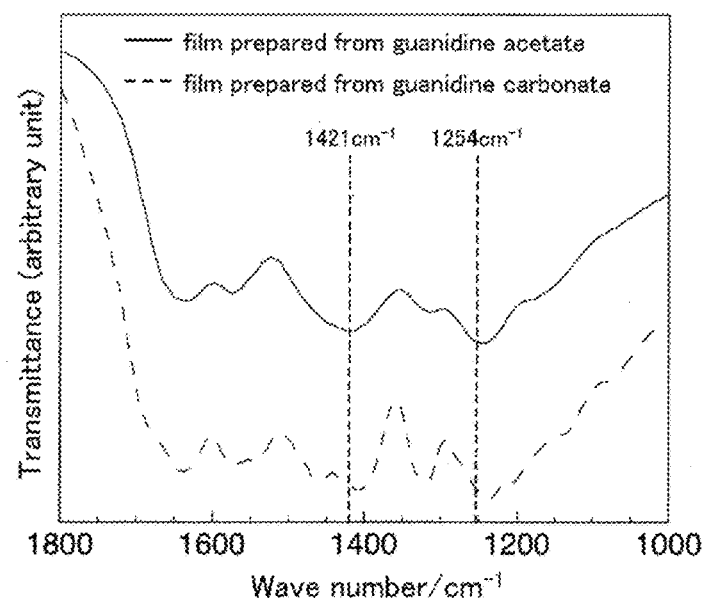
FIG. 16 is a graph showing the result of IR spectrum measurement in Test Example 13.

Further, the obtained IR spectra are shown in FIG. 16. In the IR spectrum of the guanidine acetate, as compared to the IR spectrum of guanidine carbonate, a shift of a peak that appears to correspond to oxygen doping was observed at around 1421 $cm^{-1}$ and around 1254 $cm^{-1}$. These results indicate that the film formed from guanidine acetate is of a structure in which a melem skeleton is contained as a structural unit, but is partially oxidized and thus doped with oxygen.

Example 6

Preparation of Free-Standing Film

A film prepared on a glass substrate by the same method as in Example 1 was immersed in pure water for some time. The film separated from the substrate was transferred onto a graphite substrate and then dried at 50° C. for five minutes. This completed an intended free-standing film.

Example 7

Transfer of g-$C_3N_4$ Film

A g-$C_3N_4$ film prepared on a glass substrate by the same method as in Example 1 was spin-coated with a 0.1 w % CYTOP (registered trademark) solution for 10 seconds at 1000 rpm, was heated at 80° C. for 1 hour and then heated at 200° C. for 1 hour. Thereafter, the g-$C_3N_4$ film was immersed in pure water to be peeled off from the glass substrate. This completed the g-$C_3N_4$ film transferred onto the CYTOP polymer.

Example 8

Transfer of g-$C_3N_4$ Film

A g-$C_3N_4$ film prepared on a glassy carbon by the same method as in Example 1 was coated with a raw material of epoxy resin. After polymerization proceeded, the resin was peeled off from the substrate. This completed the g-$C_3N_4$ film transferred onto the resin.

[Test Example 14]

Photoresponsivity of g-$C_3N_4$ Film

Figure 17:
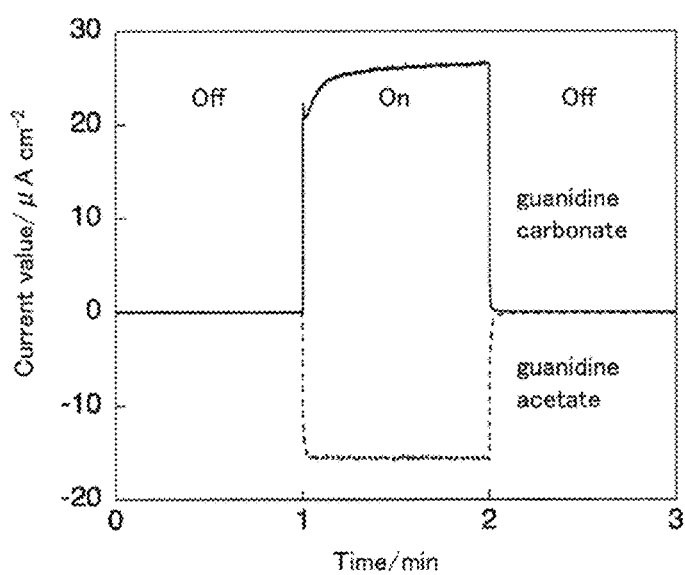
FIG. 17 is a graph showing the result of photoresponsivity in Test Example 14.

Photoresponsivity of the g-$C_3N_4$ film was evaluated with use of an optical electrode cell. A g-$C_3N_4$ film made from guanidine carbonate and formed onto a graphite substrate by the same method as in Example 4 and a g-$C_3N_4$ film made from guanidine acetate and formed onto a graphite substrate by the same method as in Example 5 were used for measurement. Platinum (Pt) was used as a counter electrode, 0.1M sodium sulfate was used as an electrolyte, an aqueous solution of 0.025M potassium hydrogenphosphate and 0.025 M sodium hydrogenphosphate was used as a pH buffer. As a light source, a 300 W xenon lamp was used for irradiation of visible light of λ>300 nm. In addition, a voltage was 0 V vs Ag/AgCl, and a photocurrent was measured. The result is shown in FIG. 17.

Regardless of whether the starting material was guanidine carbonate or guanidine acetate, photocurrents were detected from both of the g-$C_3N_4$ films, without using a sacrificial reagent. In addition, it was found that a direction in which a current flows through the g-$C_3N_4$ film obtained with use of guanidine carbonate as the starting material is opposite to a direction in which a current flows through the g-$C_3N_4$ film obtained with use of guanidine acetate as the starting material. Further, the g-$C_3N_4$ film formed with use of guanidine carbonate by the method as in Example 1 showed a result similar to that obtained for the g-$C_3N_4$ film formed on the graphite substrate with use of guanidine carbonate by the method as in Example 4 (No drawing for showing the results is provided). These results indicate that change of a counter anion can control physical properties.

Example 9

Preparation of g-C$_3$N$_4$ Film

Preparation of g-C$_3$N$_4$ films was performed with use of guanidine carbonate (2.0 g, 11.1 mmol) by the same method as in Example 1. This yielded blue films on the individual substrates.

Changing a film thickness can change a color of a film.

INDUSTRIAL APPLICABILITY

The present invention is applicable to production of a g-C$_3$N$_4$ film. A g-C$_3$N$_4$ film produced according to the present invention can be used as, for example, a photocatalyst that produces hydrogen through water photolysis.

The invention claimed is:

1. A graphitic carbon nitride film having a single-layer or multilayer sheet structure in which melem structural units are crosslinked in two-dimensional directions, wherein a peak obtained for the graphitic carbon nitride film having a multilayer sheet structure by out-of-plane X-ray diffraction is derived from a sheet-to-sheet distance only, and wherein the film does not have a reflection peak which is derived from the inter-melem skeleton and corresponds to a peak in the vicinity of 2θ=12.5°.

2. The graphitic carbon nitride film according to claim 1, wherein
the sheet-to-sheet distance is in a range from 3.17 Å to 3.26 Å.

3. The graphitic carbon nitride film according to claim 1, wherein
the graphitic carbon nitride film produces a photocurrent of not less than 0.8 μA/cm$^2$ when the graphitic carbon nitride film is irradiated with visible light of not less than 420 nm while a constant voltage of 0.2 V is applied to the graphitic carbon nitride film.

4. The graphitic carbon nitride film according to claim 1, wherein
the graphitic carbon nitride film has transparency.

5. The graphitic carbon nitride film according to claim 1, wherein
the graphitic carbon nitride film being produced by a method for producing a graphitic carbon nitride film, the method comprising the steps of:
heating, as a starting material, a compound represented by X$^+_m$Y$^+$ wherein X$^+$ is selected from a guanidium ion, a guanidine derivative ion represented by Formula (I) below, and a guanidine derivative ion represented by Formula (II) below, Y$^{m-}$ is an anion, and m is a valence of Y,

[Chem. 1]

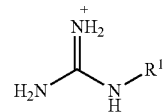

(I)

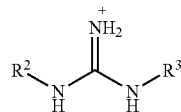

(II)

wherein, in Formulae (I) and (II), R$^1$, R$^2$, and R$^3$ are independently selected from an amino group, a nitro group, an alkyl group having 1 to 10 carbon atoms, —(C$_2$H$_4$O)$_n$—R$^4$ (where n is 1 to 10, and R$^4$ is an alkyl group having 1 to 4 carbon atoms), halogen, and a primary amide group, to vaporize the compound or its reactant; and
depositing the compound or the reactant over a surface of a base material heated, the surface carrying negative electric charges or having π electrons, so that the compound or the reactant is polymerized on the base material to generate a graphitic carbon nitride.

6. A base material having the graphitic carbon nitride film according to claim 5 fixed on a surface thereof.

7. An electrically conductive substrate having the graphitic carbon nitride film according to claim 5 fixed on a surface thereof.

* * * * *

UNITED STATES PATENT AND TRADEMARK OFFICE
CERTIFICATE OF CORRECTION

PATENT NO. : 10,252,253 B2  
APPLICATION NO. : 14/653641  
DATED : April 9, 2019  
INVENTOR(S) : Daigo Miyajima et al.

Page 1 of 1

It is certified that error appears in the above-identified patent and that said Letters Patent is hereby corrected as shown below:

In the Claims

Column 30, Claim 5, Line 5 reads:  
$X^+_m Y^+$ wherein $X^+$ is selected from a guanidium ion, a  
Whereas it should read:  
$X^+_m Y^{m-}$, wherein $X^+$ is selected from a guanidium ion, a Signed and Sealed this  
Twentieth Day of August, 2019

Andrei Iancu  
*Director of the United States Patent and Trademark Office*